US008969227B2

(12) United States Patent
Mathers et al.

(10) Patent No.: US 8,969,227 B2
(45) Date of Patent: Mar. 3, 2015

(54) ZIRCONIA-BASED MATERIAL DOPED WITH YTTRIUM AND LANTHANUM

(71) Applicant: 3M Innovative Properties Company, St. Paul, MN (US)

(72) Inventors: James P. Mathers, Woodbury, MN (US); Kathleen M. Humpal, Stillwater, MN (US); Brant U. Kolb, Afton, MN (US); Mark J. Hendrickson, Minneapolis, MN (US); Myles L. Brostrom, West Lakeland Township, MN (US); Holger Hauptmann, Sindelsdorf (DE)

(73) Assignee: 3M Innovative Properties Company, St. Paul, MN (US)

( * ) Notice: Subject to any disclaimer, the term of this patent is extended or adjusted under 35 U.S.C. 154(b) by 16 days.

(21) Appl. No.: 14/065,622

(22) Filed: Oct. 29, 2013

(65) Prior Publication Data
US 2014/0057774 A1 Feb. 27, 2014

Related U.S. Application Data

(62) Division of application No. 13/512,151, filed as application No. PCT/US2010/061489 on Dec. 21, 2010, now Pat. No. 8,598,058.

(60) Provisional application No. 61/292,220, filed on Jan. 5, 2010, provisional application No. 61/290,693, filed on Dec. 29, 2009.

(51) Int. Cl.
| C04B 35/48 | (2006.01) |
| B82Y 30/00 | (2011.01) |
| C01G 25/02 | (2006.01) |
| C04B 35/486 | (2006.01) |
| C04B 35/624 | (2006.01) |
| C04B 35/626 | (2006.01) |
| C04B 38/00 | (2006.01) |
| C04B 38/06 | (2006.01) |
| A61K 6/02 | (2006.01) |

(52) U.S. Cl.
CPC ............ *C04B 35/48* (2013.01); *A61K 6/024* (2013.01); *B82Y 30/00* (2013.01); *C01G 25/02* (2013.01); *C01P 2002/52* (2013.01); *C01P 2004/03* (2013.01); *C01P 2004/64* (2013.01); *C01P 2006/16* (2013.01); *C04B 35/486* (2013.01); *C04B 35/624* (2013.01); *C04B 35/6263* (2013.01); *C04B 35/62695* (2013.01); *C04B 38/0074* (2013.01); *C04B 38/0615* (2013.01); *C04B 2235/3225* (2013.01); *C04B 2235/3227* (2013.01); *C04B 2235/449* (2013.01); *C04B 2235/6562* (2013.01); *C04B 2235/6565* (2013.01); *C04B 2235/6567* (2013.01); *C04B 2235/762* (2013.01); *C04B 2235/765* (2013.01); *C04B 2235/77* (2013.01); *C04B 2235/785* (2013.01); *C04B 2235/9653* (2013.01)
USPC ............................................. 501/103; 106/35

(58) Field of Classification Search
CPC .............. C04B 35/486; C04B 2235/3246; A61K 6/024
USPC ............................................. 501/103; 106/35
See application file for complete search history.

(56) References Cited

U.S. PATENT DOCUMENTS

| 3,058,594 | A | 10/1962 | Hultgren |
| 4,639,356 | A | 1/1987 | O'Toole |
| 4,758,541 | A | 7/1988 | Tsukuma |
| 4,764,491 | A | 8/1988 | Quadir |
| 4,788,045 | A | 11/1988 | Colombet |
| 4,842,739 | A | 6/1989 | Tang |
| 4,985,229 | A | 1/1991 | Obitsu |
| 5,017,532 | A | 5/1991 | Sonnenberg |
| 5,037,579 | A | 8/1991 | Matchett |
| 5,453,262 | A | 9/1995 | Dawson |
| 5,468,847 | A | 11/1995 | Heilmann |
| 5,652,192 | A | 7/1997 | Matson |
| 5,849,068 | A | 12/1998 | Hofmann |
| 6,376,590 | B2 | 4/2002 | Kolb |
| 1,620,490 | A1 | 6/2004 | Castro |
| 6,887,588 | B2 | 5/2005 | Ackerman |
| 7,241,437 | B2 | 7/2007 | Davidson |
| 1,526,683 | A1 | 11/2007 | Tanaka |
| 7,364,806 | B2 | 4/2008 | Matsumoto |

(Continued)

FOREIGN PATENT DOCUMENTS

| EP | 1550644 | 7/2005 |
| EP | 1550645 | 7/2005 |
| EP | 1803686 | 7/2007 |
| EP | 2221276 | 8/2010 |
| JP | 07-187774 | 7/1995 |

(Continued)

OTHER PUBLICATIONS

Adschiri, "Rapid and Continuous Hydrothermal Crystallization of Metal Oxide Particles in Supercritical Water", Journal of the American Ceramic Society, 1992, vol. 75, No. 4, pp. 1019-1022.

(Continued)

*Primary Examiner* — Karl Group
(74) *Attorney, Agent, or Firm* — Jean A. Lown

(57) ABSTRACT

Sintered bodies containing zirconia-based ceramic materials and partially sintered bodies that are intermediates in the preparation of the sintered bodies are described. The zirconia-based ceramic material is doped with lanthanum and yttrium. The grain size of the zirconia-based ceramic material can be controlled by the addition of lanthanum. The crystalline phase of the zirconia-based ceramic material can be influenced by the addition of yttrium.

5 Claims, 11 Drawing Sheets

(56) References Cited

U.S. PATENT DOCUMENTS

| | | |
|---|---|---|
| 7,429,422 B2 | 9/2008 | Davidson |
| 7,527,761 B2 | 5/2009 | Swartzlander |
| 7,674,523 B2 | 3/2010 | Davidson |
| 8,598,058 B2 | 12/2013 | Mathers |
| 2006/0148950 A1 | 7/2006 | Davidson |
| 2010/0041542 A1 | 2/2010 | Rolf |
| 2010/0276374 A1 | 11/2010 | Kolb |
| 2011/0260349 A1 | 10/2011 | Rolf |
| 2012/0264588 A1 | 10/2012 | Kolb |

FOREIGN PATENT DOCUMENTS

| | | |
|---|---|---|
| JP | 08-033650 | 2/1996 |
| JP | 08-033701 | 2/1996 |
| JP | 2000-095564 | 4/2000 |
| WO | WO 01/30702 | 5/2001 |
| WO | WO 02/40398 | 5/2002 |
| WO | WO 2004/103907 | 12/2004 |
| WO | WO 2008/083282 | 7/2008 |
| WO | WO 2011/082031 | 7/2011 |

OTHER PUBLICATIONS

W. B. Blumenthal, The Chemical Behavior of Zirconium, Chapter 8, "Carboxylates of Zirconium", pp. 311-338, D. Van Nostrand Company, Inc., Princeton, NJ, (1958).

Chaim, "Effect of Oxide Additives on Grain Growth During Sintering of Nanocrystalline Zirconia Alloys", Materials Letters, May 1998, vol. 35, pp. 245-250.

Dawson, "Hydrothermal Synthesis of Advanced Ceramic Powders", Ceramic Bulletin, 1988, vol. 67, No. 10, pp. 1673-1678.

Hakuta, "Hydrothermal Synthesis of Zirconia Nanocrystals in Supercritical Water", J. Materials Research, Aug. 2004, vol. 19, No. 8, pp. 2230-2234.

Hwang, "Grain Size Control of Tetragonal Zirconia Polycrystals Using the Space Charge Concept", Journal of the American Ceramic Society, Nov. 1990, vol. 73, No. 11, pp. 3269-3277.

Kim, "Lattice Parameters, Iconic Conductivities, and Solubility Limits in Fluorite-Structure $MO_2$ Oxide ($M=Hf^{4+}$, $Zr^{4+}$, $Ce^{4+}$, $Th^{4+}$, $U^{4+}$) Solid Solutions", Journal of the American Ceramic Society, 1989, vol. 72, No. 8, pp. 1415-1421.

Liu, "$La_2O_3$-modified YSZ Coatings: High-temperature Stability and Improved Thermal Barrier Properties", Surface & Coatings Technology, Jan. 15, 2009, vol. 203, No. 8, pp. 1014-1019.

Matsumoto, "Thermal Cycle Behavior of Plasma Sprayed $La_2O_3$, $Y_2O_3$ Stabilized $ZrO_2$ Coatings", Scripta Materialia, Jun. 2006, vol. 54, No. 12, pp. 2035-2039.

Ogihara, "Continuous Processing of Monodispersed Titania Powders", Journal of the American Ceramic Society, Sep. 1989, vol. 72, No. 9, pp. 1598-1601.

Speakman, "Development of Proton Conductors Using Pyrochlore-Perovskite Phase Boundaries", Journal of Materials Engineering and Performance, Jun. 2004, vol. 13, No. 3, pp. 303-308.

International Search Report for PCT/US2010/061489, 4 pages, Mar. 2011.

ZIRCONIA-BASED MATERIAL DOPED WITH YTTRIUM AND LANTHANUM

CROSS REFERENCE TO RELATED APPLICATION

This application is a Divisional application of prior U.S. application Ser. No. 13/512,151, filed May 25, 2012, now U.S. Pat. No. 8,598,058, which is a national state filing under 35 U.S.C. §371 of International Application No. PCT/US2010/061489, filed Dec. 21, 2010, which claims benefit of U.S. Provisional Application Nos. 61/292,220, filed Jan. 5, 2010 and 61/290,693, filed Dec. 29, 2009, the disclosures of which are incorporated by reference herein in their entireties.

TECHNICAL FIELD

Zirconia-based material doped with both yttrium and lanthanum is described.

BACKGROUND

Ceramic materials prepared from various metal oxides have been used in diverse applications. These ceramic materials can be prepared by first forming a green body that contains metal oxide particles. The green body is subsequently sintered to consolidate the particles into a dense body and to achieve the desired final properties.

Many ceramic materials are aluminum-based or silicon-based. Some zirconia-based ceramics have also been prepared. Compared to other ceramic materials, zirconia-based ceramics can have improved mechanical strength associated with a phase transformation mechanism that can be triggered when a crack propagates into the ceramic material. More specifically, tetragonal phase zirconia can be transformed to monoclinic phase zirconia under such conditions. The formation of the monoclinic phase tends to arrest the progression of the crack throughout the ceramic material.

SUMMARY

Zirconia-based materials that contain zirconia, yttrium, and lanthanum are described. These materials are typically in the form of particles, green bodies, partially sintered bodies, or sintered bodies. The sintered bodies, which have an average grain size that is less than or equal to 200 nanometers, can be used in a variety of applications such as those where toughness and optical translucency are desired. Methods of making the sintered bodies are also described.

In a first aspect, a sintered body is provided. The sintered body contains a zirconia-based ceramic material that contains 92.5 to 98.0 mole percent zirconium oxide, 1.5 to 2.5 mole percent yttrium oxide, and 0.5 to 5.0 mole percent lanthanum oxide based on total moles of inorganic oxide in the zirconia-based ceramic material. The zirconia-based ceramic material has an average grain size less than or equal to 200 nanometers.

In a second aspect, a method of making a sintered body that includes a zirconia-based ceramic material is provided. The method includes providing a zirconia-based sol that contains zirconia-based particles that are crystalline and that have an average particle size no greater than 100 nanometers. The zirconia-based particles contain at least 92.5 mole percent zirconium oxide, at least 1.5 mole percent yttrium oxide, and at least 0.5 mole percent lanthanum oxide based on total moles of inorganic oxide in the zirconia-based particles. The method further includes forming a zirconia-based green body from the zirconia-based sol such that the green body contains at least 25 volume percent inorganic oxide based on a total volume of the green body. The method still further includes heating the zirconia-based green body to sinter the zirconia-based particles and to form the zirconia-based ceramic material. The zirconia-based ceramic material has an average grain size that is no greater than 200 nanometers.

In a third aspect, a partially sintered body is provided. The partially sintered body includes a product formed by partially sintering zirconia-based particles. The zirconia-based particles are crystalline and have an average particle size no greater than 100 nanometers. The zirconia-based particles contain at least 92.5 mole percent zirconium oxide, at least 1.5 mole percent yttrium oxide, and at least 0.5 mole percent lanthanum oxide based on total moles of inorganic oxide in the zirconia-based particles. The partially sintered body includes 25 to 75 volume percent inorganic oxide and 25 to 75 volume percent voids based on a total volume of the partially sintered body.

The above summary is not intended to describe every embodiment or every implementation of the present invention. The description that follows more particularly exemplifies illustrative embodiments and implementations. In several places through the description, guidance is provided through lists of examples, which can be used in various combinations. In each instance, unless stated to the contrary, the recited list serves only as a representative group and should not be interpreted as an exclusive list.

BRIEF DESCRIPTION OF DRAWINGS

FIG. 6b is a field emission scanning micrograph of a fracture surface for a sintered body of Example 15a.

DETAILED DESCRIPTION

Figure 1:
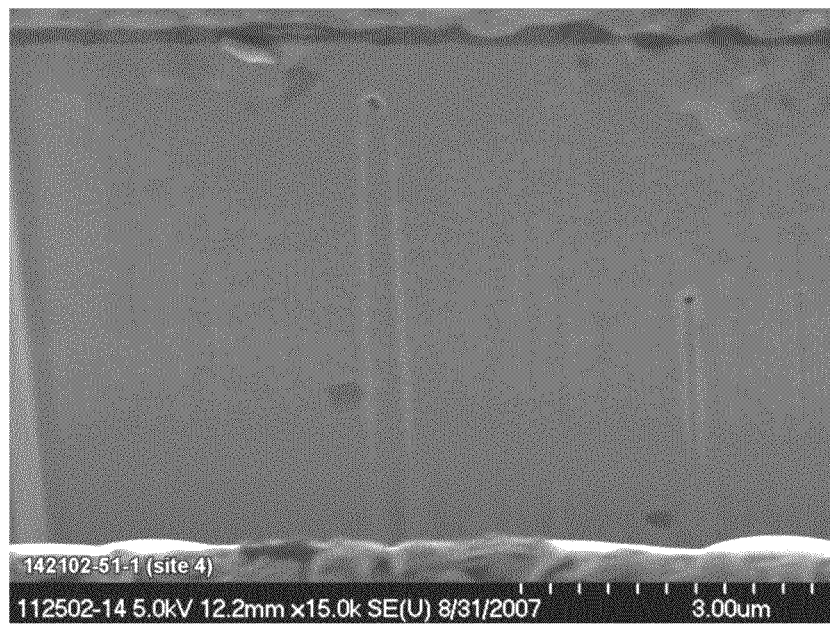
FIG. 1 is a field emission scanning micrograph of an ion-milled cross section of a sintered zirconia-based material. The material was prepared by further sintering a partially sintered zirconia block that is commercially available under the trade designation LAVA from 3M ESPE (Saint Paul, Minn.). The pores (i.e. voids) shown in the micrograph are circled.

Sintered bodies containing zirconia-based ceramic materials as well as green bodies and partially sintered bodies that are intermediates in the preparation of the sintered bodies are described. The zirconia-based ceramic material in the sintered bodies contains zirconium, yttrium, and lanthanum. The grain size of the zirconia-based ceramic material can be controlled by the addition of lanthanum. The crystalline phase of the zirconia-based ceramic material can be influenced by the addition of yttrium. Methods of making the sintered bodies are also described.

As used herein, the term "a", "an", and "the" are used interchangeably with "at least one" to mean one or more of the element being described.

As used herein, the term "zirconia" refers to various stoichiometric formulas for zirconium oxide. The most typical stoichiometeric formula is $ZrO_2$, which is generally referred to as either zirconium oxide or zirconium dioxide.

As used herein, the term "zirconia-based" means that the majority of the material is zirconia. For example, at least 70 mole percent, at least 80 mole percent, at least 90 mole percent, or at least 92.5 mole percent of the particles or ceramic material is zirconia. The zirconia is typically doped with other inorganic materials such as, for example, yttrium and lanthanum. These other inorganic materials are typically present in the form of an inorganic oxide. Various organic molecules can be sorbed on the surface of the particles or ceramic material.

As used herein, the term "inorganic oxide" includes, but is not limited to, oxides of various inorganic elements such as, for example, zirconium oxide, yttrium oxide, and lanthanum oxide.

As used herein, the term "translucent" refers to a material that is at least partially transparent to visible wavelengths of light when the material is crushed and screened to a particle size in the range of 150 to 300 micrometers and when viewed at 50 times magnification with incident light.

As used herein, the term "in the range" includes the endpoints of the range and all numbers between the endpoints. For example, in the range of 1 to 10 includes the numbers 1 and 10 as well as all numbers between 1 and 10.

As used herein, the term "hydrothermal" refers to a method of heating an aqueous medium to a temperature above the normal boiling point of the aqueous medium at a pressure that is equal to or greater than the pressure required to prevent boiling of the aqueous medium.

A sintered body is provided that includes a zirconia-based ceramic material. As used herein, the term "sintered body" refers to a ceramic material having greater than 75 volume percent inorganic oxide and less than 25 volume percent voids. The zirconia-based ceramic material is prepared by sintering zirconia-based particles having an average diameter no greater than 100 nanometers. The zirconia-based particles are crystalline and include zirconia doped with both yttrium and lanthanum. That is, the zirconia-based particles contain zirconium oxide, yttrium oxide, and lanthanum oxide.

The zirconia-based ceramic material typically has an average grain size that is less than or equal to 200 nanometers. The small gain size results from the use of zirconia-based particles to prepare the sintered body that are in the nanoparticle size range plus from the addition of lanthanum to these particles. The grain size is often less than or equal to 175 nanometers, less than or equal to 150 nanometers, or less than or equal to 125 nanometers. The small grain size can advantageously lead to sintered bodies that can be translucent. In applications where translucency of the sintered body is desirable, the average grain size is often less than or equal to 100 nanometers, less than or equal to 90 nanometers, less than or equal to 80 nanometers, less than or equal to 70 nanometers, less than or equal to 60 nanometers, or less than or equal to 50 nanometers.

At least 92.5 mole percent of the inorganic oxide in the zirconia-based ceramic material is zirconia. Often, at least 93 mole percent, at least 93.5 mole percent, at least 94 mole percent, at least 94.5 mole percent, at least 95 mole percent, at least 95.5 mole percent, at least 96 mole percent of the inorganic oxide in the zirconia-based ceramic material is zirconia. The amount of zirconia can be up to 98 mole percent, up to 97.5 mole percent, up to 97 mole percent, or up to 96.5 mole percent. For example, the amount of zirconia can be in the range of 92.5 to 98 mole percent, in the range of 93 to 98 mole percent, in the range of 94 to 98 mole percent, in the range of 95 to 98 mole percent, in the range of 93 to 97 mole percent, in the range of 93 to 96 mole percent, or in the range of 93 to 95 mole percent.

The zirconia in the zirconia-based ceramic material is crystalline. The crystalline material is typically cubic, tetragonal, or monoclinic. Because the cubic and tetragonal phases are difficult to differentiate using x-ray diffraction techniques, these two phases are typically combined for quantitative purposes and are referred to as the cubic/tetragonal phase. The term "cubic/tetragonal" or "C/T" are used interchangeably to refer to the cubic plus the tetragonal crystalline phases. The percent cubic/tetragonal phase can be determined, for example, by measuring the peak area of the x-ray diffraction peaks for each phase and using Equation (I).

$$\% \text{ C/T} = 100(\text{C/T}) \div (\text{C/T} + M) \quad \text{(I)}$$

In Equation (I), C/T refers to the peak area of the diffraction peak for the cubic/tetragonal phase, M refers to the peak area of the diffraction peak for the monoclinic phase, and % C/T refers to the weight percent cubic/tetragonal crystalline phase. The details of the x-ray diffraction measurements are described more fully in the Example section below.

A large percentage of the tetragonal phase (e.g., the cubic/tetragonal phase) is often desired. Zirconia-based ceramic material that is present in the tetragonal phase can undergo transformation toughening when fractured. That is, a portion of the tetragonal phase material can be transformed to monoclinic phase material in the region of the fracture. The monoclinic phase material tends to occupy a larger volume than the tetragonal phase material. This transformation tends to arrest the propagation of the fracture.

In many embodiments, at least 80 percent of the zirconia-based ceramic material in the sintered body as initially prepared is present in the cubic/tetragonal crystalline phase. That is, as initially prepared, at least 80 percent, at least 85 percent, at least 90 percent, at least 95 percent, at least 98 percent, at least 99 percent, or at least 99.5 percent of the zirconia-based ceramic material is present in the cubic/tetragonal crystalline phase. The remainder of the zirconia-based ceramic material is typically present in the monoclinic crystalline phase. Stated in terms of the amount of monoclinic phase, less than 20 percent of the zirconia in the zirconia-based ceramic material as initially prepared is present in the monoclinic phase.

The zirconia-based ceramic material in the sintered body as initially prepared is typically 80 to 100 percent cubic/tetragonal and 0 to 20 percent monoclinic, 85 to 100 percent cubic/tetragonal and 0 to 15 percent monoclinic, 90 to 100 percent cubic/tetragonal and 0 to 10 percent monoclinic, or 95 to 100 percent cubic/tetragonal and 0 to 5 percent monoclinic.

When the zirconia-based ceramic material is crushed, the amount of monoclinic crystalline phase tends to increase. For example, the amount of monoclinic phase can increase up to 25 percent or more. Stated differently, the amount of cubic/tetragonal crystalline phase can decrease up to 25 percent or more. The decrease in cubic/tetragonal crystalline phase, for example, can be up to 20 percent, up to 15 percent, up to 10 percent. In some instances, the decrease is not greater than 10 percent. For example, the decrease can be up to 8 percent, up to 6 percent, or up to 5 percent. The decrease in the amount of cubic/tetragonal crystalline phase can be, for example, in the range of 1 to 10 percent, in the range of 2 to 10 percent, in the range of 4 to 10 percent, or in the range of 6 to 10 percent. In cases where the zirconia-based ceramic material is prepared with more than 1 mole percent lanthanum oxide, a separate phase of lanthanum zirconate phase can form.

After crushing, the zirconia-based ceramic material in the sintered body is often 70 to 99 percent cubic/tetragonal and 1 to 30 percent monoclinic, 70 to 95 percent cubic/tetragonal and 5 to 30 percent monoclinic, 80 to 99 percent cubic/tetragonal and 1 to 20 percent monoclinic, 80 to 95 percent cubic/tetragonal and 5 to 20 percent monoclinic, or 90 to 99 percent cubic/tetragonal and 1 to 10 percent monoclinic.

The zirconia-based ceramic material typically includes an amount of yttrium oxide in a range of 1.5 to 2.5 mole percent based on a total number of moles of inorganic oxide in the zirconia-based ceramic material. The yttrium oxide tends to enhance the stability of the metastable tetragonal phase. If less than 1.5 mole percent yttrium oxide is included in the zirconia-based ceramic material of the sintered body as initially prepared, a greater amount of the monoclinic phase tends to form during cooling of the sintered body from the sintering temperature to room temperature. Stresses related to the volume expansion associated with the transformation from the tetragonal phase to the monoclinic phase can spontaneously fracture the sintered body while cooling. The end result can be a sintered body that is fractured. If greater than 2.5 mole percent yttrium oxide is include in the zirconia-based ceramic material of the sintered body as initially prepared, however, the tetragonal phase may be so stable that the resulting sintered body often cannot undergo transformation toughening when subjected to stress after formation (i.e., after sintering and cooling to room temperature). That is, a greater amount of yttrium oxide tends to stabilize the tetragonal phase to such an extent that little or no monoclinic phase can be formed when the zirconia-based ceramic material is fractured during use. The exact amount of yttrium oxide desired in the zirconia-based ceramic material depends on the grain size. Smaller grain sizes tend to contribute to the stability of the tetragonal phase. Therefore, as the grain size becomes smaller, less yttrium oxide is required to achieve the optimum level of tetragonal phase stability.

The zirconia-based ceramic material often includes at least 1.5 mole percent, at least 1.6 mole percent, at least 1.7 mole percent, at least 1.8 mole percent, at least 1.9 mole percent, or at least 2.0 mole percent yttrium oxide based on total moles of inorganic oxide present in the zirconia-based ceramic material. The amount of yttrium oxide is often up to 2.5 mole percent, up to 2.4 mole percent, up to 2.3 mole percent, or up to 2.1 mole percent. For example, the amount of yttrium oxide can be in the range of 1.5 to 2.5 mole percent, in the range of 1.5 to 2.4 mole percent, in the range of 1.5 to 2.3 mole percent, in the range of 1.5 to 2.2 mole percent, in the range of 1.5 to 2.1 mole percent, in the range of 1.5 to 2.0 mole percent, in the range of 1.6 to 2.5 mole percent, in the range of 1.7 to 2.5 mole percent, in the range of 1.8 to 2.5 mole percent, in the range of 1.9 to 2.5 mole percent, or in the range of 2.0 to 2.5 mole percent. A separate yttrium-containing phase is typically not detected using x-ray diffraction methods.

The zirconia-based ceramic material typically includes an amount of lanthanum oxide in a range of 0.5 to 5 mole percent based on total moles of inorganic oxide in the zirconia-based ceramic material. Lanthanum oxide tends to influence the grain size of the zirconia-based ceramic material. If less than 0.5 mole percent lanthanum oxide is present, the grain size tends to be larger than 200 nanometers. Grain sizes larger than 200 nanometers tend to result in zirconia-based ceramic materials with increased opaqueness. Smaller grain sizes tend to result in zirconia-based ceramic materials with greater translucency or less opaqueness. If the lanthanum oxide is increased to an amount greater than 5 mole percent, however, there often is no further visual improvement in translucency.

The amount of lanthanum oxide is often at least 0.5 mole percent, at least 0.75 mole percent, at least 1.0 mole percent, at least 1.25 mole percent, at least 1.5 mole percent, at least 1.75 mole percent, at least 2 mole percent, at least 2.25 mole percent, at least 2.5 mole percent, at least 2.75 mole percent, or at least 3 mole percent based on total moles of inorganic oxide in the zirconia-based ceramic material. The amount can be up to 5.0 mole percent, up to 4.75 mole percent, up to 4.5 mole percent, up to 4.25 mole percent, up to 4.0 mole percent, up to 3.75 mole percent, or up to 3.5 mole percent. The lanthanum oxide can be present in an amount in the range of 0.5 to 5.0 mole percent, in the range of 1.0 to 5.0 mole percent, in the range of 1.5 to 5.0 mole percent, in the range of 2.0 to 5.0 mole percent, in the range of 2.5 to 5.0 mole percent, in the range of 0.5 to 4.5 mole percent, in the range of 0.5 to 4.0 mole percent, in the range of 0.5 to 3.5 mole percent, or in the range of 0.5 to 3.0 mole percent. A separate lanthanum phase is typically not detected in the sintered body using x-ray diffraction methods when the concentration is below 1 mole percent. If the concentration of lanthanum is greater than 1 mole percent in the sintered body, however, a separate lanthanum-containing phase can often be detected.

The zirconia-based ceramic material typically contains 92.5 to 98.0 mole percent zirconium oxide, 1.5 to 2.5 mole percent yttrium oxide, and 0.5 to 5.0 mole percent lanthanum oxide based on the total moles of the inorganic oxide. For example, the zirconia-based ceramic material can include 94 to 98 mole percent zirconium oxide, 1.5 to 2.5 mole percent yttrium oxide, and 0.5 to 4.5 mole percent lanthanum oxide. In another example, the zirconia-based ceramic material can include 94 to 98 mole percent zirconium oxide, 1.5 to 2.5 mole percent yttrium oxide, and 0.5 to 3.5 mole percent lanthanum oxide. In yet another example, the zirconia-based ceramic material can include 94.5 to 97.5 mole percent zirconium oxide, 1.5 to 2.5 mole percent yttrium oxide, and 1.0 to 3.0 mole percent lanthanum oxide. In still another example, the zirconia-based ceramic material can include 94.7 to 97.1 mole percent zirconium oxide, 1.9 to 2.3 mole percent yttrium oxide, and 1.0 to 3.0 mole percent lanthanum oxide.

The sintered body has relatively few pores. The pores in the sintered body can be detected, for example, by focused ion milling a trench into the ceramic material and viewing the trench using field emission scanning electron microscopy. This method is further described in the Example section. The average size of the pores can be calculated from their average diameter. The pores that are present in the sintered body tend to have an average pore size (i.e., average diameter) no greater than 100 nanometers. For example, the average pore size can be no greater than 80 nanometers, no greater than 60 nanometers, no greater than 50 nanometers, or no greater than 40 nanometers. In some sintered bodies, the average pore size is in the range of 10 to 100 nanometers, in the range of 20 to 100 nanometers, in the range of 10 to 80 nanometers, in the range of 20 to 80 nanometers, in the range of 10 to 60 nanometers, in the range of 20 to 60 nanometers, in the range of 25 to 75 nanometers, or in the range of 25 to 50 nanometers.

The sintered body contains greater than 75 volume percent inorganic oxide and less than 25 volume percent voids (i.e., pores) based on the total volume of the sintered body. In some examples, the sintered body contains greater than 80 volume percent inorganic oxide and less than 20 volume percent voids, greater than 90 volume percent inorganic oxide and less than 10 volume percent voids, greater than 95 volume percent inorganic oxide and less than 5 volume percent voids, greater than 98 volume percent inorganic oxide and less than 2 volume percent voids, or greater than 99 volume percent inorganic oxide and less than 1 volume percent voids.

If the sintered body has no pores (i.e., voids), it is considered to have the maximum density possible for that material. This maximum density possible is referred to as the "theoretical density". If pores are present in the sintered body, the density is less than the theoretical value. The percentage of the theoretical density can be determined from electron micrographs of a cross-section of the sintered body. The percent of the area of the sintered body in the electron micrograph that is attributable to pores can be calculated. Stated differently, the percent of the theoretical density can be calculated by subtracting the percent voids from 100 percent. That is, if 2 percent of the area of the electron micrograph of the sintered body is attributable to pores, the sintered body is considered to have a density equal to 98 percent of the theoretical density. This method is further described in the Example section.

As the density approaches the theoretical density, the translucency of the zirconia-based sintered body tends to improve. In many embodiments, the sintered body has a density that is at least 99 percent of the theoretical value. For example, the density can be at least 99.2 percent, at least 99.5 percent, at least 99.6 percent, at least 99.7 percent, at least 99.8 percent, at least 99.9 percent, or at least 99.95 percent of the theoretical density. In some sintered bodies, no pores can be detected. Sintered bodies with a density that is at least 99 percent of the theoretical density often appear translucent to the human eye. A material with lower porosity can appear more opaque than a material with higher porosity if the pores are larger. That is, a sintered body with a density of 99 percent of the theoretical value can seem more translucent than a sintered body with a density of 99.5 percent of the theoretical value if the average pore size is smaller for the lower density material.

A method of making a sintered body that includes a zirconia-based ceramic material is provided. The method includes providing a zirconia-based sol that contains zirconia-based particles. These particles are crystalline and have an average particle size no greater than 100 nanometers. The zirconia-based particles contain at least 92.5 mole percent zirconium oxide, at least 1.5 mole percent yttrium oxide, and at least 0.5 mole percent lanthanum oxide based on total moles of inorganic oxide in the zirconia-based particles. The method further includes forming a zirconia-based green body from the zirconia-based sol such that the green body contains at least 25 volume percent inorganic oxide based on a total volume of the green body. The method still further includes heating the zirconia-based green body to sinter the zirconia-based particles and to form the zirconia-based ceramic material. The zirconia-based ceramic material has an average grain size that is no greater than 200 nanometers.

Any known method can be used to provide the zirconia-based sol that contains zirconia-based particles having an average particle size no greater than 100 nanometers. In many embodiments, a hydrothermal method is used to provide this sol from a feedstock that contains dissolved zirconium salts, dissolved yttrium salts, and dissolved lanthanum salts in an aqueous medium. Hydrothermal technology can be used to prepare zirconia-based particles that are crystalline and non-associated. As used herein, the term "non-associated" refers to particles that are free or substantially free from aggregation and/or agglomeration.

The zirconium salts, yttrium salts, and lanthanum salts in the feedstock are dissolved in water or a mixture of water with other water soluble or miscible materials. The dissolved salts are typically chosen to be removable during subsequent processing steps and to be non-corrosive. The dissolved salts are typically carboxylate salts. Although any carboxylate anion can be used, the carboxylate anion often has no greater than 4 carbon atoms such as, for example, formate, acetate, propionate, butyrate, or a combination thereof. The dissolved salts are often acetate salts. The feedstock can further include the corresponding carboxylic acid of the carboxylate anion. For example, feedstocks prepared from acetate salts often contain acetic acid.

At least a majority of the dissolved salts in the feedstock are usually carboxylate salts rather than halide salts, oxyhalide salts, nitrate salts, or oxynitrate salts. Halide and nitrate anions in the feedstock tend to result in the formation of zirconia-based particles that are predominately of a monoclinic phase rather than the more desirable tetragonal or cubic phases. Further, carboxylates and/or acids thereof tend to be more compatible with an organic matrix material compared to halides and nitrates.

In many embodiments, the dissolved zirconium salt is zirconium acetate salt. Zirconium acetate can be represented by a formula such as $ZrO_{((4-n)/2)}{}^{n+}(CH_3COO^-)_n$ where n is in the range of 1 to 2. The zirconium ion may be present in a variety of structures depending, for example, on the pH of the feedstock. Methods of making zirconium acetate are described, for example, in W. B. Blumenthal, "The Chemical Behavior of Zirconium," pp. 311-338, D. Van Nostrand Company, Princeton, N.J. (1958). Suitable aqueous solutions of zirconium acetate are commercially available, for example, from Magnesium Elektron, Inc. (Flemington, N.J.) that contain up to 17 weight percent zirconium, up to 18 weight percent zirconium, up to 20 weight percent zirconium, up to 22 weight percent, up to 24 weight percent, up to 26 weight percent, or up to 28 weight percent zirconium based on the total weight of the solution.

Similarly, the dissolved yttrium salt can be yttrium acetate and the dissolved lanthanum salt can be lanthanum acetate. These salts are commercially available from a variety of manufacturers. Because the yttrium and lanthanum salts are used at much lower concentration levels than the zirconium salt, salts other than carboxylate salts (e.g., acetate salts) can be selected. For example, either or both of the yttrium salts and lanthanum salts can be a nitrate salt.

The amount of the various salts dissolved in the feedstock can be readily determined based on the total percent solids selected for the feedstock. The relative amounts of the various salts can be calculated to provide the selected percent solids and to prepare zirconia-based material that contains at least 92.5 mole percent zirconium oxide ($ZrO2$), at least 1.5 mole percent yttrium oxide ($Y_2O_3$), and at least 0.5 mole percent lanthanum oxide ($La_2O_3$). Each mole percent is based on the total moles of inorganic oxide in the zirconia-based material.

Typically, the feedstock is a solution and does not contain dispersed or suspended solids. For example, seed particles usually are not present in the feedstock. The feedstock usually contains greater than 5 weight percent solids and these solids are typically dissolved. As used herein, the "weight percent solids" is calculated by drying a sample at 120° C. and refers the portion of the feedstock that is not water, a water-miscible co-solvent, or another compound that can be vaporized at temperatures up to 120° C. The weight percent solids is equal to 100(dry weight)÷(wet weight).

In this equation, the term "wet weight" refers to the weight of a feedstock sample before drying and the term "dry weight" refers to the weight of the sample after drying, for example, at 120° C. for at least 30 minutes.

In many embodiments, the feedstock contains greater than 5 weight percent, greater than 10 weight percent, greater than 12 weight percent, or greater than 15 weight percent solids. Some feedstocks contain up to 25 weight percent solids or higher. For example, the feedstock can contain up to 24 weight percent, up to 22 weight percent, up to 20 weight percent, or up to 19 weight percent solids. Some exemplary feedstocks have solids in the range of 10 to 25 weight percent, 12 to 22 weight percent, 14 to 20 weight percent, or 15 to 19 weight percent.

When subjected to hydrothermal treatment, the various dissolved salts in the feedstock undergo hydrolysis and condensation reactions to form the zirconia-based particle. These reactions are often accompanied with the release of an acidic byproduct. That is, the byproduct is often one or more carboxylic acids corresponding to the zirconium carboxylate salt plus any yttrium carboxylate salt and lanthanum carboxylate salt in the feedstock. For example, if the salts are zirconium acetate, yttrium acetate, and lanthanum acetate, acetic acid is formed as a byproduct of the hydrothermal reaction.

Any suitable hydrothermal reactor can be used for the preparation of the zirconia-based particles. The reactor can be a batch or continuous reactor. The heating times are typically shorter and the temperatures are typically higher in a continuous hydrothermal reactor compared to a batch hydrothermal reactor. The time of the hydrothermal treatments can be varied depending on the type of reactor, the temperature of the reactor, and the concentration of the feedstock. The pressure in the reactor can be autogeneous (i.e., the vapor pressure of water at the temperature of the reactor), can be hydraulic (i.e., the pressure caused by the pumping of a fluid against a restriction), or can result from the addition of an inert gas such as nitrogen or argon. Suitable batch hydrothermal reactors are available, for example, from Parr Instruments Co. (Moline, Ill.). Some suitable continuous hydrothermal reactors are described, for example, in U.S. Pat. Nos. 5,453,262 (Dawson et al.) and 5,652,192 (Matson et al.); Adschiri et al., *J. Am. Ceram. Soc.*, 75, 1019-1022 (1992); and Dawson, *Ceramic Bulletin*, 67 (10), 1673-1678 (1988).

If a batch reactor is used to form zirconia-based particles, the temperature is often in the range of 160° C. to 275° C., in the range of 160° C. to 250° C., in the range of 170° C. to 250° C., in the range of 175° C. to 250° C., in the range of 200° C. to 250° C., in the range of 175° C. to 225° C., in the range of 180° C. to 220° C., in the range of 180° C. to 215° C., or in the range of 190° C. to 210° C. The feedstock is typically placed in the batch reactor at room temperature. The feedstock within the batch reactor is heated to the designated temperature and held at that temperature for at least 30 minutes, at least 1 hour, at least 2 hours, or at least 4 hours. The temperature can be held up to 24 hours, up to 20 hours, up to 16 hours, or up to 8 hours. For example, the temperature can be held in the range of 0.5 to 24 hours, in the range of 1 to 18 hours, in the range of 1 to 12 hours, or in the range of 1 to 8 hours. Any size batch reactor can be used. For example, the volume of the batch reactor can be in a range of several milliliters to several liters or more.

In many embodiments, the feedstock is passed through a continuous hydrothermal reactor. As used herein, the term "continuous" with reference to the hydrothermal reactor system means that the feedstock is continuously introduced and an effluent is continuously removed from the heated zone. The introduction of feedstock and the removal of the effluent typically occur at different locations of the reactor. The continuous introduction and removal can be constant or pulsed.

Figure 11:
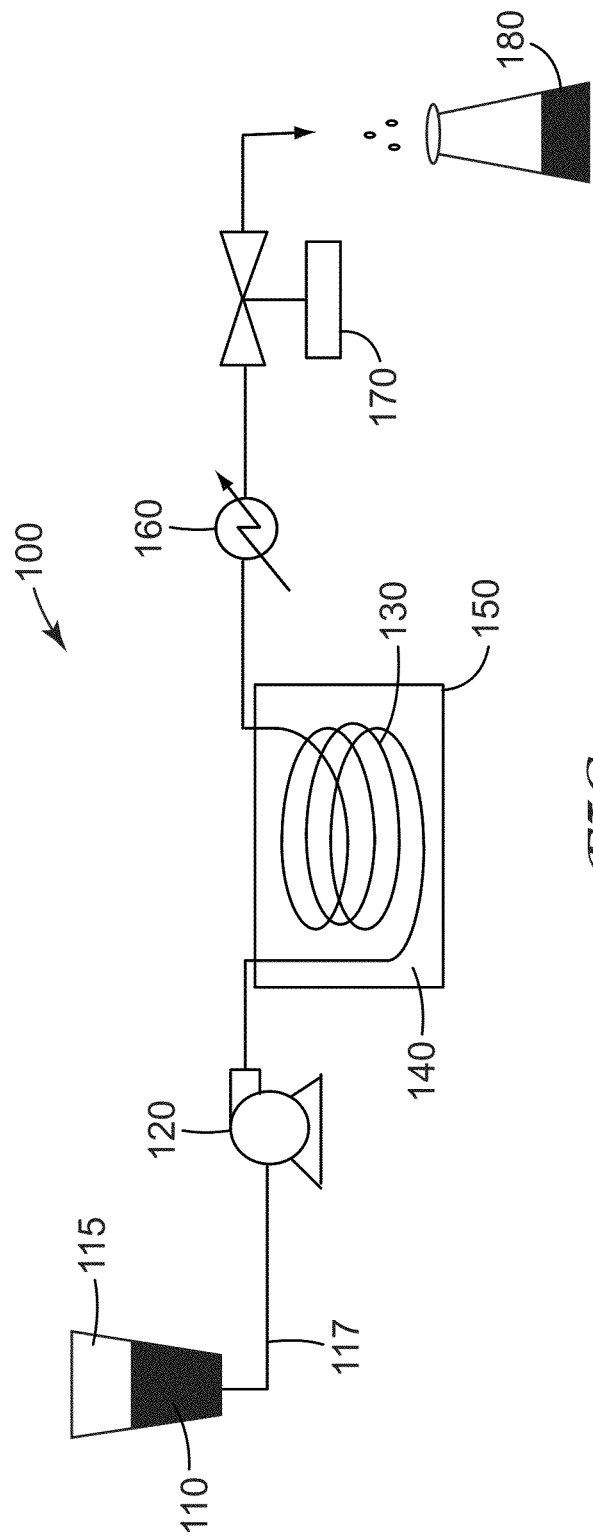
FIG. 11 is a schematic representation of an exemplary continuous hydrothermal reactor system that can be used to prepare the zirconia-based particles.

One exemplary continuous hydrothermal reactor system 100 is shown schematically in FIG. 11. The feedstock 110 is contained within a feedstock tank 115. The feedstock tank is connected with tubing or piping 117 to a pump 120. Similar tubing or piping can be used to connect other components of the tubular reactor system. The tubing or piping 117 can be constructed of any suitable material such as metal, glass, ceramic, or polymer. The tubing or piping 117 can be, for example, polyethylene tubing or polypropylene tubing in the portions of the continuous hydrothermal reactor system 100 that are not heated and that are not under high pressure. Any tubing that is heated or under pressure is often made of metal (e.g., stainless steel, carbon steel, titanium, nickel, or the like) or has a metal outer housing. The pump 120 is used to introduce the feedstock 110 into the tubular reactor 130. That is, the pump 120 is connected to the inlet of the tubular reactor 130. Any type of pump 120 can be used that is capable of pumping against the pressure within the tubular reactor 130. The pump can provide a constant or pulsed flow of the feedstock solution into the tubular reactor 130. As used herein, the term "tubular reactor" refers to the portion of the continuous hydrothermal reactor system that is heated (i.e., the heated zone). Although the tubular reactor 130 is shown in FIG. 11 as a coil of tubing, the tubular reactor can be in any suitable shape. The shape of the tubular reactor is often selected based on the desired length of the tubular reactor and the method used to heat the tubular reactor. For example, the tubular reactor can be straight, U-shaped, or coiled. The interior potion of the tubular reactor can be empty or can contain baffles, balls, or other known mixing means.

As shown in FIG. 11, the tubular reactor 130 is placed in a heating medium 140 within a heating medium vessel 150. The heating medium 140 can be, for example, an oil, sand, salt, or the like that can be heated to a temperature above the hydrolysis and condensation temperatures of the metal salts. Suitable oils include, for example, plant oils such as peanut oil and canola oil. Some plant oils are preferably kept under nitrogen when heated to prevent or minimize oxidation of the oils. Other suitable oils include polydimethylsiloxanes such as those commercially available from Duratherm Extended Fluids (Lewiston, N.Y.) under the trade designation "DURATHERM S". Suitable salts include, for example, sodium nitrate, sodium nitrite, potassium nitrate, or mixtures thereof. The heating medium vessel 150 can be any suitable container that can hold the heating medium and that can withstand the heating temperatures used for the tubular reactor 130. The heating medium vessel 150 can be heated using any suitable means. In many embodiments, the heating medium vessel 150 is positioned inside an electrically heated coil. Alternatively, other types of heaters such as, for example, induction heaters, microwave heaters, fuel-fired heaters, heating tape, and steam coils can be used in place of the heating vessel 150, the heating medium 140, or both.

The tubular reactor 130 can be made of any material capable of withstanding the temperatures and pressures used to prepare zirconia particles. The tubular reactor 130 preferably is constructed of a material that can resist dissolution in an acidic environment. For example, carboxylic acids can be present in the feedstock or can be produced as a reaction byproduct within the continuous hydrothermal reactor system. In some exemplary embodiments, the tubular reactor is made of stainless steel, nickel, titanium, carbon-based steel, or the like.

In other exemplary embodiments, an interior surface of the tubular reactor contains a fluorinated polymeric material. This fluorinated polymeric material can include, for example, a fluorinated polyolefin. In some embodiments, the polymeric material is polytetrafluoroethylene (PTFE) such as TEFLON, which is a trade designation of DuPont (Wilmington, Del.). Some tubular reactors have a fluorinated polymeric hose such as a TEFLON hose within a metal housing such as a braided stainless steel housing. The fluorinated polymeric surface is particularly advantageous for use with feedstocks and/or reaction products that contain carboxylic acids. These carboxylic acids can leach metals from some known hydrothermal reactors such as those constructed of stainless steel.

The second end of the tubular reactor 130 is usually connected to a cooling device 160. Any suitable cooling device 160 can be used. In some embodiments, the cooling device 160 is a heat exchanger that includes a section of tubing or piping that has an outer jacket filled with a cooling medium such as cool water. In other embodiments, the cooling device 160 includes a coiled section of tubing or piping that is placed in a vessel that contains cooling water. In either of these embodiments, the tubular reactor effluent is passed through the section of tubing and is cooled from the tubular reactor temperature to a temperature no greater than 100° C., no greater than 80° C., no greater than 60° C., or no greater than 40° C. Other cooling devices that contain dry ice or refrigeration coils can also be used. After cooling, the reactor effluent can be discharged into a product collection vessel 180. The reactor effluent is preferably not cooled below the freezing point prior to being discharged into the product collection vessel 180.

The pressure inside the tubular reactor can be at least partially controlled with a backpressure valve 170, which is generally positioned between the cooling device 160 and the sample collection vessel 180. The backpressure valve 170 controls the pressure at the exit of the continuous hydrothermal reactor system 100 and helps to control the pressure within the tubular reactor 130. The backpressure is often at least 100 pounds per square inch (0.7 MPa), at least 200 pounds per square inch (1.4 MPa), at least 300 pounds per square inch (2.1 MPa), at least 400 pounds per square inch (2.8 MPa), at least 500 pounds per square inch (3.5 MPa), at least 600 pounds per square inch (4.2 MPa), or at least 700 pounds per square inch (4.9 MPa). The backpressure should be high enough to prevent boiling within the tubular reactor.

The dimensions of the tubular reactor 130 can be varied and, in conjunction with the flow rate of the feedstock, can be selected to provide suitable residence times for the reactants within the tubular reactor. Any suitable length tubular reactor can be used provided that the residence time and temperature are sufficient to convert the zirconium in the feedstock to zirconia-based particles. The tubular reactor often has a length of at least 0.5 meter, at least 1 meter, at least 2 meters, at least 5 meters, at least 10 meters, at least 15 meters, at least 20 meters, at least 30 meters, at least 40 meters, or at least 50 meters. The length of the tubular reactor in some embodiments is less than 500 meters, less than 400 meters, less than 300 meters, less than 200 meters, less than 100 meters, less than 80 meters, less than 60 meters, less than 40 meters, or less than 20 meters.

Tubular reactors with a relatively small inner diameter are typically preferred. For example, tubular reactors having an inner diameter no greater than about 3 centimeters are often used because of the fast rate of heating of the feedstock that can be achieved with these reactors. Also, the temperature gradient across the tubular reactor is less for reactors with a smaller inner diameter compared to those with a larger inner diameter. The larger the inner diameter of the tubular reactor, the more this reactor resembles a batch reactor. However, if the inner diameter of the tubular reactor is too small, there is an increased likelihood of the reactor becoming plugged or partially plugged during operation resulting from deposition of material on the walls of the reactor. The inner diameter of the tubular reactor is often at least 0.1 centimeters, at least 0.15 centimeters, at least 0.2 centimeters, at least 0.3 centimeters, at least 0.4 centimeters, at least 0.5 centimeters, or at least 0.6 centimeters. In some embodiments, the diameter of the tubular reactor is no greater than 3 centimeters, no greater than 2.5 centimeters, no greater than 2 centimeters, no greater than 1.5 centimeters, or no greater than 1.0 centimeters. Some tubular reactors have an inner diameter in the range of 0.1 to 3.0 centimeters, in the range of 0.2 to 2.5 centimeters, in the range of 0.3 to 2 centimeters, in the range of 0.3 to 1.5 centimeters or in the range of 0.3 to 1 centimeters.

In a continuous hydrothermal reactor, the temperature and the residence time are selected in conjunction with the tubular reactor dimensions to convert at least 90 mole percent of the zirconium in the feedstock to zirconia-based particles using a single hydrothermal treatment. That is, at least 90 mole percent of the dissolved zirconium in the feedstock is converted to zirconia-based particles within a single pass through the continuous hydrothermal reactor system.

Alternatively, a multiple step hydrothermal process can be used. For example, the feedstock can be subjected to a first hydrothermal treatment to form a zirconium-containing intermediate and a by-product such as a carboxylic acid. A second feedstock can be formed by removing at least a portion of the by-product of the first hydrothermal treatment from the zirconium-containing intermediate. The second feedstock can then be subjected to a second hydrothermal treatment to form a sol containing the zirconia-based particles. This process is further described in U.S. Pat. No. 7,241,437 (Davidson et al.).

If a two step hydrothermal process is used, the percent conversion of the zirconium-containing intermediate is typically 40 to 75 mole percent. The conditions used in the first hydrothermal treatment can be adjusted to provide conversion within this range. Any suitable method can be used to remove at least part of the by-product of the first hydrothermal treatment. For example, carboxylic acids such as acetic acid can be removed by a variety of methods such as vaporization, dialysis, ion exchange, precipitation, filtration, and the like.

When referring to a continuous hydrothermal reactor, the term "residence time" means the average length of time that the feedstock is within the heated portion of the continuous hydrothermal reactor system. For the reactor depicted in FIG. 11, the residence time is the average time the feedstock is within the tubular reactor 130 and is equal to the volume of the tubular reactor divided by the flow rate of the feedstock through the tubular reactor. The residence time in the tubular reactor can be varied by altering the length or diameter of the tubular reactor as well as by altering the flow rate of the feedstock. In many embodiments, the residence time is at least 1 minute, at least 2 minutes, at least 4 minutes, at least 6 minutes, at least 8 minutes, or at least 10 minutes. The residence time is typically no greater than 240 minutes, no greater than 180 minutes, no greater than 120 minutes, no greater than 90 minutes, no greater than 60 minutes, no greater than 45 minutes, or no greater than 30 minutes. In many examples, the residence time is in the range of 1 to 240 minutes, in the range of 1 to 180 minutes, in the range of 1 to 120 minutes, in the range of 1 to 90 minutes, in the range of 1 to 60 minutes, in the range of 10 to 90 minutes, in the range of 10 to 60 minutes, in the range of 20 to 60 minutes, or in the range of 30 to 60 minutes.

Any suitable flow rate of the feedstock through the tubular reactor can be used as long as the residence time is sufficiently long to convert the dissolved zirconium to zirconia-based particles. That is, the flow rate is often selected based on the residence time needed to convert the zirconium in the feedstock to zirconia-based particles. Higher flow rates are desirable for increasing throughput and for minimizing the deposition of materials on the walls of the tubular reactor. A higher flow rate can often be used when the length of the reactor is increased or when both the length and diameter of the reactor are increased. The flow through the tubular reactor can be either laminar or turbulent.

In some exemplary continuous hydrothermal reactors, the reactor temperature is in the range of 170° C. to 275° C., in the range of 170° C. to 250° C., in the range of 170° C. to 225° C., in the range of 180° C. to 225° C., in the range of 190° C. to 225° C., in the range of 200° C. to 225° C., or in the range of 200° C. to 220° C. If the temperature is greater than about 275° C., the pressure may be unacceptably high for some hydrothermal reactors systems. However, if the temperature is less than about 170° C., the conversion of the zirconium in the feedstock to zirconia-based particles may be less than 90 weight percent using typical residence times.

The effluent of the hydrothermal treatment (i.e., the product of the hydrothermal treatment) is a zirconia-based sol. As used herein, the term "sol" refers to a dispersion or suspension of the zirconia-based particles in an aqueous-based medium. The zirconia-based sol contains zirconia-based particles having an average particle size no greater than 100 nanometers. The zirconia-based particles contain at least 92.5 mole percent zirconium oxide, at least 1.5 mole percent yttrium oxide, and at least 0.5 mole percent lanthanum oxide. In many embodiments, the zirconia-based particles contain 92.5 to 98.0 mole percent zirconium oxide, 1.5 to 2.5 mole percent yttrium oxide, and 0.5 to 5.0 mole percent lanthanum oxide. The average particle size of the zirconia-based particles is no greater than 100 nanometers.

In the process of preparing the sintered body, a zirconia-based green body is formed from the zirconia-based sol. As used herein, the term "green body" refers to an article prepared from the zirconia-based sol by removal of at least some of the liquid phase. That is, the zirconia-based sol is concentrated to form the green body. The green body typically has at least 25 volume percent inorganic oxide. In addition to inorganic oxide, the green body can include a liquid phase, voids, unreacted salts that were in the feedstock, byproducts of the hydrothermal conversion reaction, and the like. Any suitable concentration method can be used to form the green body. Although the zirconia-based sol may be subjected to a drying step in the process of forming the green body, the zirconia-based particles within the green body are typically not sintered. Any drying temperature used to form the green body is typically less than 400° C., less than 300° C., less than 200° C., or less than 100° C.

The green body typically has at least 25 volume percent, at least 30 volume percent, at least 35 volume percent, at least 40 volume percent, or at least 45 volume percent inorganic oxide. The volume percent inorganic oxide can be up to 50 volume percent or even higher. For example, the green body can be in a range of 25 to 50 volume percent, in the range of 25 to 45 volume percent, 25 to 40 volume percent solids, or 25 to 35 volume percent inorganic oxide. The concentration methods used to form the green body typically results in the drawing together of the zirconia-based particles through capillary forces during concentration. The individual zirconia-based particles are typically held together by van der Waals forces or by an organic material such as an organic binder.

In one exemplary concentration method to form the green body, the zirconia-based sol can be subjected to osmotic casting. A sample of the zirconia-based sol can be positioned within a membrane bag that is closed and then placed within a bath of a solution of a poly(alkylene oxide) such as poly(ethylene glycol). The aqueous medium diffuses out of the zirconia-based sol within the membrane bag. That is, the aqueous medium diffuses out of the zirconia-based sol through the membrane bag and into the bath to equalize the concentration of water or water-soluble components within the membrane bag to that in the bath. The bath can be replaced periodically to further lower the concentration of the aqueous medium within the membrane bag. A membrane bag is typically selected that allows diffusion of water, carboxylic acids and/or anions thereof but that does not allow diffusion of the zirconia-based particles out of the membrane bag and that does not allow diffusion of the bath (e.g., poly(alkylene oxide) solution) into the membrane bag. Upon removal of at least a portion of the aqueous medium, the zirconia-based sol tends to become a gel. This gel can then be dried in an oven, such as in an oven set at a temperature in the range of 40° C. to 150° C., in the range of 40° C. to 120° C., in the range of 40° C. to 100° C., or in the range of 40° C. to 80° C. to from the green body. The green body has at least 25 volume percent, at least 30 volume percent, or at least 35 volume percent inorganic oxide.

In another exemplary method, the zirconia-based sol can be subjected to distillation or to both distillation and drying for concentration purposes. For example, the zirconia-based sol can be concentrated to about 10 to 15 volume percent inorganic oxide using distillation methods and then further concentrated to at least 25 volume percent inorganic oxide based on the total volume of the resulting green body.

The carboxylic acid and/or carboxylate anions optionally can be removed from the zirconia-based sol prior to concentration. For example, dialysis or diafiltration can be used to remove at least a portion of the dissolved carboxylic acids and/or carboxylate anions thereof. For dialysis, a sample of the zirconia-based sol can be positioned within a membrane bag that is closed and then placed within a water bath. The carboxylic acid and/or carboxylate anions diffuse out of the sample within the membrane bag. That is, these species can diffuse out of the effluent through the membrane bag into the water bath to equalize the concentration within the membrane bag to the concentration in the water bath. The water in the bath is typically replaced several times to lower the concentration of species within the bag. A membrane bag is typically selected that allows diffusion of the carboxylic acids and/or carboxylate anions thereof but does not allow diffusion of the zirconia-based particles out of the membrane bag.

For diafiltration, a permeable membrane is used to filter the sample. The zirconia particles can be retained on the filter if the pore size of the filter is appropriately chosen. The dissolved carboxylic acids and/or carboxylate anions thereof pass through the filter. Any liquid that passes through the filter is replaced with fresh water. In a discontinuous diafiltration process, the sample is often diluted to a pre-determined volume and then concentrated back to the original volume by ultrafiltration. The dilution and concentration steps are repeated one or more times until the carboxylic acid and/or carboxylate anions thereof are removed or lowered to an acceptable concentration level. In a continuous diafiltration process, which is often referred to as a constant volume diafiltration process, fresh water is added at the same rate that liquid is removed through filtration. The dissolved carboxylic acid and/or anions thereof are in the liquid that is removed.

Either dialysis or ultrafiltration can be used to remove the carboxylic acid in the aqueous medium and the dissolved carboxylate anions. Even after such treatments, however, some residual carboxylic acid can be sorbed on the surface of the zirconia-based particles.

The zirconia-based particles within the green body are sintered to form the sintered body. The green body is typically heated at a controlled rate to the desired sintering temperature and then held at the sintering temperature for a time sufficient for sintering to occur. For example, the temperature can be increased at a rate of 1° C./minute to 200° C./minute, at a rate of 5° C./minute to 100° C./minute, at a rate of 10° C./minute to 100° C./minute, or at a rate of 10° C./minute to 50° C./minute. The sintering temperature can be held for any suitable amount of time such as at least 1 minute, at least 5 minutes, at least 10 minutes, at least 30 minutes, at least 60 minutes, at least 2 hours, at least 3 hours, or at least 4 hours. The sintered body is then cooled to room temperature. The rate of cooling is often controlled.

Any desired sintering temperature can be selected to form the sintered body. If the sintering temperature is too low, however, sintering may not be complete and residual pores can remain. These residual pores may weaken the sintered body and may also negatively impact translucency. If the sintering temperature is too high, however, the grain size tends to increase. An increased grain size may also negatively impact translucency. In many embodiments the sintering temperature can be in the range of 1000° C. to 1250° C. The sintering process is typically done in air.

Depending on the final use of the sintered body, the green body can optionally be pulverized or broken up into a desired granule size prior to sintering or partial sintering.

A partially sintered body is provided. The partially sintered body includes a product formed by partially sintering zirconia-based particles. The zirconia-based particles are crystalline and have an average particle size no greater than 100 nanometers. The zirconia-based particles contain at least 92.5 mole percent zirconium oxide, at least 1.5 mole percent yttrium oxide, and at least 0.5 mole percent lanthanum oxide based on total moles of inorganic oxide in the zirconia-based particles. The partially sintered body includes 25 to 75 volume percent inorganic oxide and 25 to 75 volume percent voids based on a total volume of the partially sintered body.

In some applications, it may be desirable to form a partially sintered body. As used herein, the term "partially sintered body" refers to a material that is intermediate between the green body and the sintered body. The partially sintered body is often formed from the zirconia-based green body. The partially sintered body typically contains no more than 75 volume percent inorganic oxide and at least 25 volume percent voids. The partially sintered body can have more mechanical integrity than the green body. For example, some green bodies tend to crumble apart when handled and cannot be machined to another shape. The partially sintered body, however, can be machined and typically does not crumble when handled. Because it has a lower density, the partially sintered body can be more readily machined than a sintered body to a desired shape. That is, the partially sintered body can be shaped to the desired shape before complete sintering.

The partially sintered body usually includes 25 to 75 volume percent inorganic oxide based on a total volume of the partially sintered body. For example, the partially sintered body can have at least 25 volume percent, at least 30 volume percent, at least 35 volume percent, at least 40 volume percent, or at least 45 volume percent inorganic oxide. The partially sintered body can have up to 75 volume percent, up to 70 volume percent, up to 65 volume percent, or up to 60 volume percent inorganic oxide. In some embodiments, the partially sintered body can include 30 to 75 volume percent, 35 to 75 volume percent, 40 to 75 volume percent, 30 to 70 volume percent, 30 to 60 volume percent, 40 to 70 volume percent, or 40 to 60 volume percent inorganic oxide. The inorganic oxide contains at least 92.5 mole percent zirconium oxide, at least 1.5 mole percent yttrium oxide, and at least 0.5 mole percent lanthanum oxide.

In addition to the inorganic oxide, the partially sintered body typically includes voids. For example, the partially sintered body can include 25 to 75 volume percent voids based on the total volume of the partially sintered body. Often, all or most of the volume of the partially sintered body that is not attributable to the inorganic solids is attributable to voids. Usually, all or almost all (e.g., at least 90 percent or more, at least 95 percent or more, at least 98 percent or more, or at least 99 percent or more) of the liquid phase that was present in the zirconia-based sol has been removed in the formation of the partially sintered body. Likewise, all or almost all of any carboxylic acid byproduct of the hydrothermal treatment has been removed in the formation of the partially sintered body.

In some embodiments, the partially sintered body can include 25 to 75 volume percent inorganic oxide and 25 to 75 volume percent voids, 30 to 75 volume percent inorganic and 25 to 70 volume percent voids, 40 to 75 volume percent inorganic oxide and 25 to 60 volume percent voids, 30 to 70 volume percent inorganic oxide and 30 to 70 volume percent voids, 30 to 60 volume percent inorganic oxide and 40 to 70 volume percent voids, or 40 to 60 volume percent inorganic oxide and 40 to 60 volume percent voids.

The inorganic oxide in the partially sintered body originates from the zirconia-based particles used to form the green body. The zirconia-based particles and the inorganic oxide in the partially sintered body contain at least 92.5 mole percent zirconium oxide, at least 1.5 mole percent yttrium oxide, and at least 0.5 mole percent lanthanum oxide. In many embodiments, the zirconia-based particles and the inorganic oxide in the partially sintered body contain 92.5 to 98.0 mole percent zirconium oxide, 1.5 to 2.5 mole percent yttrium oxide, and 0.5 to 5.0 mole percent lanthanum oxide.

The partially sintered body can be prepared from the green body using a combination of sintering time and temperature to provide 25 to 75 volume percent inorganic oxide and 25 to 75 volume percent voids based on a total volume of the partially sintered body. The partially sintered body typically has been exposed to a temperature equal to at least 400° C. For example, the temperature can be in the range of 400° C. to 1100° C. The time and temperature combination is selected to partially sinter the zirconia-based particles together. The extent of sintering is selected to be sufficient to provide the desired mechanical integrity and density to the partially sintered body. Similarly to the formation of the sintered body, the temperature can to be increased to the desired temperature at a controlled rate and can be decreased from the desired temperature at a controlled rate.

The partially sintered body can be further sintered to form the sintered body. The sintered body can be used for many applications where tough ceramic material is desired. For example, the sintered body can be used in various dental applications.

Various items are provided including, for example, a sintered body, a method of making a sintered body, or a partially sintered body.

A first item is provided that is a sintered body. The sintered body contains a zirconia-based ceramic material that contains 92.5 to 98.0 mole percent zirconium oxide, 1.5 to 2.5 mole percent yttrium oxide, and 0.5 to 5.0 mole percent lanthanum oxide based on total moles of inorganic oxide in the zirconia-based ceramic material. The zirconia-based ceramic material has an average grain size less than or equal to 200 nanometers.

A second item is provided that can be a version of the first item. In the second item, the sintered body has a density that is at least 99 percent of a theoretical density.

A third item is provided that can be a version of the first item. In the third item, the sintered body has a density that is at least 99.5 percent of a theoretical density.

A fourth item is provided that can be a version of the first item. In the fourth item, the sintered body has a density that is at least 99.9 percent of a theoretical density.

A fifth item is provided that can be a version of the first to fourth item. In the fifth item, the average grain size is less than or equal to 100 nanometers.

A sixth item is provided that can be a version of the first to fifth item. In the sixth item, at least 70 percent of the zirconia-based ceramic material has a cubic/tetragonal crystalline structure.

A seventh item is provided that can be a version of the first to fifth item. In the seventh item, at least 80 percent of the zirconia-based ceramic material has a cubic/tetragonal crystalline structure.

An eighth item is provided that can be a version of the first to seventh item. In the eighth item, the sintered body has an average pore size no greater than 100 nanometers.

A ninth item is provided that can be a version of the first to seventh item. In the ninth item, the sintered body has an average pore size no greater than 50 nanometers.

A tenth item is provided that can be a version of the first to ninth item. In the tenth item, the zirconia-based ceramic material contains 94.7 to 97.1 mole percent zirconium oxide, 1.9 to 2.3 mole percent yttrium oxide, and 1.0 to 3.0 mole percent lanthanum oxide.

An eleventh item is provided that is a method of making a sintered body. The method includes providing a zirconia-based sol that contains zirconia-based particles that are crystalline and that have an average particle size no greater than 100 nanometers. The zirconia-based particles contain at least 92.5 mole percent zirconium oxide, at least 1.5 mole percent yttrium oxide, and at least 0.5 mole percent lanthanum oxide based on total moles of inorganic oxide in the zirconia-based particles. The method further includes forming a zirconia-based green body from the zirconia-based sol such that the green body contains at least 25 volume percent inorganic oxide based on a total volume of the green body. The method still further includes heating the zirconia-based green body to sinter the zirconia-based particles and to form the zirconia-based ceramic material. The zirconia-based ceramic material has an average grain size that is no greater than 200 nanometers.

A twelfth item is provided that can be a version of the eleventh item. In the twelfth item, forming the zirconia-based green body includes osmotic casting.

A thirteenth item is provided that can be a version of the eleventh or twelfth item. In the thirteenth item, the method further includes preparing a partially sintered body from the green body such that the partially sintered body comprises 25 to 75 volume percent inorganic oxide and 25 to 75 volume percent voids. Further, sintering includes heating the partially sintered body to form the sintered body comprising greater than 75 volume percent inorganic oxide and less than 25 volume percent voids.

A fourteenth item is provided that is a partially sintered body. The partially sintered body includes a product formed by partially sintering zirconia-based particles. The zirconia-based particles are crystalline and have an average particle size no greater than 100 nanometers. The zirconia-based particles contain at least 92.5 mole percent zirconium oxide, at least 1.5 mole percent yttrium oxide, and at least 0.5 mole percent lanthanum oxide based on total moles of inorganic oxide in the zirconia-based particles. The partially sintered body includes 25 to 75 volume percent inorganic oxide and 25 to 75 volume percent voids based on a total volume of the partially sintered body.

A fifteenth item is provided that can be a version of the fourteenth item. In the fifteenth item, the partially sintered body contains 0 to less than 5 volume percent organic material, water, or a combination thereof.

A sixteenth item is provided that can be a version of the fourteenth or fifteenth item. In the sixteenth item, the partially sintered body comprises 40 to 70 volume percent inorganic oxide and 30 to 60 volume percent voids.

EXAMPLES

These examples are for illustrative purposes only and are not meant to be limiting on the scope of the appended claims. All parts, percentages, and ratios in the examples are by weight unless otherwise noted. Solvents and other reagents used can be obtained from Sigma-Aldrich Chemical Company (Milwaukee, Wis.) unless otherwise noted.

TABLE 1

Glossary of materials

| Abbreviation or Trade Designation | Description |
|---|---|
| Zirconium acetate | An aqueous solution of zirconium acetate nominally containing 16.3 weight percent zirconium. The solution is commercially available from Magnesium Elektron (Flemington, NJ). |
| DI water | Deionized water |
| Yttrium acetate hydrate | Y(CH$_3$COO)$_3$•4H2O that is commercially available from AMR Technologies, Inc. (Toronto, Canada). |
| Lanthanum (III) acetate | La(CH$_3$COO)$_3$•1.5 H2O that is available from Alfa Aesar (Wardhill, MA). |

Test Methods
Field Emission Scanning Electron Microscopy (FESEM)

Samples were prepared by sprinkling sintered granules onto conductive tape attached to a scanning electron microscope stub. A thin layer of Au—Pd was deposited to make the particles conductive. The microscope used was a Hitachi S-4700 field emission scanning electron microscope, which is available from Hitachi (Maidenhead, UK). Images (i.e., electron micrographs) were obtained while operating at 2.0 kilovolts and with a magnification of 70,000 times.

Line Intercept Analysis

FESEM micrographs with 70,000 times magnification were used for grain size measurement. Three or four micrographs taken from different areas of the sintered body were used for each sample. Ten horizontal lines, which were spaced at roughly equal intervals across the height of each micrograph, were drawn. The number of grain boundary intercepts observed on each line were counted and used to calculate the average distance between intercepts. The average distance for each line was multiplied by 1.56 to determine the grain size and this value was averaged over all the lines for all micrographs of each sample.

Focused Ion Beam Milling (FIB)

Samples were prepared by mounting sintered granules (i.e., sintered bodies) onto conductive tape attached to a scanning electron microscope stub. Focused ion beam milling was used to create trenches in individual granules. The trenches were approximately 25 micrometers long by 5 micrometers deep. The ion mill is commercially available under the trade designation Quanta 3D FEB from FEI Company (Hillsboro, Oreg.).

A thin layer of Au—Pd was deposited to make the samples conductive. The cross-section was examined for each sample with 5 images provided across each trench with little or no overlap. The microscope used was a Hitachi S-4700 field emission scanning electron microscope, which is available from Hitachi (Maidenhead, UK). Images were obtained while operating at 2.0 kilovolts and with a magnification of 20,000 times.

X-Ray Diffraction

Samples of sintered bodies were examined without any further changes. Reflection geometry data were collected in the form of a survey scan by use of a Bruker D8 Advance diffractometer from Bruker (Madison, Wis.) with copper $K_\alpha$ radiation, and Vantec detector registry of the scattered radiation. The diffractometer was fitted with variable incident beam slits and fixed diffracted beam slits. The survey scan was conducted in the coupled continuous mode from 10 to 80 degrees (2θ) using a 0.015 degree step size and 2 second dwell time. The x-ray generator settings of 40 kilovolts and 40 milliamps were employed.

The observed diffraction peaks were identified by comparison to the reference diffraction patterns contained within the International Center for Diffraction Data (ICDD) powder diffraction database (sets 1-47, ICDD, Newton Square, Pa.) and attributed to cubic (C), tetragonal (T), or monoclinic (M) phases of zirconia. The (111) peak was used for the cubic phase, the (101) peak was used for the tetragonal phase, and the (−111) and (111) peaks were used for the monoclinic phase. Because of the small crystalline size of the particles as prepared in the sol, the (111) peak for the cubic phase and the (101) peak for the tetragonal phase could not be separated. The phases are reported together as the C(111)/T(101) peak. The amounts of each zirconia phase were evaluated on a relative basis and the form of zirconia having the most intense diffraction peak was assigned the relative intensity value of 100. The strongest line of the remaining crystalline zirconia phase was scaled relative to the most intense line and given a value between 1 and 100.

Peak widths for the observed diffraction maxima due to corundum were measured by profile fitting. The relationship between mean corundum peak widths and corundum peak position (2θ) was determined by fitting a polynomial to these data to produce a continuous function used to evaluate the instrumental breadth at any peak position within the corundum testing range. Peak widths for the observed diffraction maxima due to zirconia were measured by profile fitting the observed diffraction peaks.

A Pearson VII peak shape model with $K_{\alpha 1}$ and $K_{\alpha 2}$ wavelength components accounted for, and linear background model were employed in all cases. Widths were found as the peak full width at half maximum (FWHM) having units of degrees. The profile fitting was accomplished by use of the capabilities of the JADE diffraction software suite.

Sample peaks were corrected for instrumental broadening by interpolation of instrumental breadth values from corundum instrument calibration and corrected peak widths converted to units of radians. The Scherrer equation was used to calculate the primary crystal size.

$$\text{Crystallite Size}(D) = K\lambda/\beta(\cos\theta)$$

In the Scherrer equation, K is the form factor (here 0.9), λ is the wavelength (1.540598 Å), β is the calculated peak width after correction for instrumental broadening (in radians), and θ equals half the peak position (scattering angle). β is equal to [calculated peak FWHM—instrumental breadth] (converted to radians) where FWHM is full width at half maximum.

The weighted average of the cubic/tetragonal (C/T) and monoclininc phases (M) were calculated using the following equation.

$$\text{Weighted average} = [(\% C/T)(C/T \text{ size}) + (\% M)(M \text{ size})]/100$$

In this equation, % C/T equals the percent crystallinity contributed by the cubic and tetragonal crystallite content of the $ZrO_2$ particles; C/T size equals the size of the cubic and tetragonal crystallites; % M equals the percent crystallinity contributed by the monoclinic crystallite content of the $ZrO_2$ particles; and M size equals the size of the monoclinic crystallites.

Hot-Stage X-Ray Diffraction Procedure

Hot stage experiments were conducted using a Panalytical (Westborough, Mass.) vertical goniometer equipped with a platinum strip furnace and Anton Pan (Graz, Austria) HTK temperature controller. The diffractometer used copper $K_\alpha$ radiation, was fitted with variable incident slits, fixed diffracted beam slits, and graphite diffracted beam monochromator, and used proportional detector registry of the scattered radiation.

Portions of samples were applied to the platinum strip furnace as fine powders (smaller than 100 mesh). Samples were heated from 30° C. at a heating rate of 150° C. per minute to each target temperature (900° C., 1000° C., 1100° C., or 1200° C.), held at the target temperature for 10 minutes, and then cooled to 30° C. at a cooling rate of 150° C. per minute.

All reflection geometry scans were conducted at 30° C. from 10 to 40 degrees (2θ) using a 0.04 degree step size and 10 second dwell time. The x-ray generator settings of 40 kilovolts and 35 milliamps were used.

Photon Correlation Spectroscopy (PCS)

Particle size measurements were made using a Zeta Sizer-nano Series, Model ZEN3600 instrument equipped with a red laser having a wavelength of 633 nanometer. This instrument is commercially available from Malvern Instruments Inc. (Westborough, Mass.). The measurements were performed in 1 centimeter square polystyrene cuvettes. The samples were prepared by adding approximately 1 grams of deionized water and several drops (about 0.1 grams) of the sol sample being analyzed into the cuvette. The contents of each sample cuvette was drawn into a clean pipet and released several times for mixing purposes. Each sample cuvette was placed in the instrument and equilibrated at 25° C.

The instrument parameters were set as follows: dispersant refractive index 1.330, dispersant viscosity 1.0019 mPa-second, material refractive index 2.10, and material absorption value 0.10 units. The automatic size-measurement procedure was then run. The instrument automatically adjusted the laser-beam position and attenuator setting to obtain the best measurement of particle size.

The ZEN3600 instrument illuminated the sample with a laser and analyzed the intensity fluctuations of the light scattered from the particles at an angle of 173 degrees. The method of Photon Correlation Spectroscopy (PCS) was used by the instrument to calculate the particle size. PCS used the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

Examples 1-8 and Comparative Examples 1-2

Examples 1-8 and Comparative Examples 1-2 were prepared as follows. The precursor solutions were prepared by combining zirconium acetate, yttrium acetate, lanthanum acetate, and deionized (DI) water with stirring (see Table 2 below). The resulting solutions (about 12 grams) were placed into general purpose acid digestion bombs with Teflon cups (Parr Model No. 4749 available from Parr Instrument Company (Moline, Ill.)). Each acid digestion bomb was placed in a forced air oven at a temperature of 225° C. for 4 hours. In some cases, several 12 gram batches of the same sol were made and then combined to form the sample. Stable crystalline sols were obtained. As used herein, the term "stable" in reference to a sol means that less than 10 weight percent of the inorganic oxide settled in one week.

Each sol was used as prepared except for Example 5 and Example 6. Example 5 was dialyzed for 20 hours (Spectra/Por Dialysis membrane MWCO 12-14,000 available from Spectrum Laboratories, Inc. (Rancho Dominguez Calif.)) and then concentrated to approximately 39 weight percent via distillation. Example 6 was concentrated to 44.5 weight percent via distillation and filtered using a 1 micron glass micro fiber membrane filter (Acrodisc 25 millimeter syringe filter available from Pall Corporation (Port Washington, N.Y.)).

The mole percents shown in Table 2 are calculated based on the concentration of the zirconium, lanthanum, and yttrium salts included in the feedstock. Typically, about 65 to 66 weight percent of the lanthanum oxide remains in the sol following dialysis or diafiltration. Accordingly, the actual lanthanum oxide concentrations in Examples 5 and 6 are lower than the values shown in Table 2. Characterization of the particles in the above sols is shown in Table 3.

TABLE 2

Examples 1-8 and Comparative Examples 1-2

| | Precursor | | | | | Sol | |
|---|---|---|---|---|---|---|---|
| | Components | Wt (grams) | Solids Percent | Temp (° C.) | Time (hours) | Oxides | Mole Percent |
| Comparative Example 1 | Zr Acetate | 10 | 19 | 225 | 4 | $ZrO_2$ | 97.8 |
| | Y Acetate | 0.269 | | | | $Y_2O_3$ | 2.2 |
| | La Acetate | 0 | | | | $La_2O_3$ | 0 |
| | DI water | 9.48 | | | | | |
| Comparative Example 2 | Zr Acetate | 100 | 19 | 225 | 4 | $ZrO_2$ | 97.5 |
| | Y Acetate | 2.69 | | | | $Y_2O_3$ | 2.2 |
| | La Acetate | 0.3109 | | | | $La_2O_3$ | 0.25 |
| | DI water | 99.17 | | | | | |
| Example 1 | Zr Acetate | 100 | 19 | 225 | 4 | $ZrO_2$ | 97.3 |
| | Y Acetate | 2.69 | | | | $Y_2O_3$ | 2.1 |
| | La Acetate | 0.6162 | | | | $La_2O_3$ | 0.5 |
| | DI water | 99.43 | | | | | |
| Example 2 | Zr Acetate | 50 | 19 | 225 | 4 | $ZrO_2$ | 96.8 |
| | Y Acetate | 1.345 | | | | $Y_2O_3$ | 2.2 |
| | La Acetate | 0.625 | | | | $La_2O_3$ | 1.0 |
| | DI water | 47.48 | | | | | |
| Example 3 | Zr Acetate | 50 | 19 | 225 | 4 | ZrO2 | 95.9 |
| | Y Acetate | 1.345 | | | | $Y_2O_3$ | 2.2 |
| | La Acetate | 1.25 | | | | $La_2O_3$ | 2.0 |
| | DI water | 49.05 | | | | | |
| Example 4 | Zr Acetate | 100 | 19 | 225 | 4 | $ZrO_2$ | 94.9 |
| | Y Acetate | 2.69 | | | | $Y_2O_3$ | 2.2 |
| | La Acetate | 3.84 | | | | $La_2O_3$ | 3.0 |
| | DI water | 103 | | | | | |
| Example 5 | Zr Acetate | 100 | 19 | 225 | 4 | $ZrO_2$ | 94.9 |
| | Y Acetate | 2.69 | | | | $Y_2O_3$ | 2.2 |
| | La Acetate | 3.84 | | | | $La_2O_3$ | 3.0 |
| | DI water | 103 | | | | | |
| Example 6 | Zr Acetate | 1200 | 19 | 225 | 4 | $ZrO_2$ | 96.8 |
| | Y Acetate | 32.28 | | | | $Y_2O_3$ | 2.2 |
| | La Acetate | 15 | | | | $La_2O_3$ | 1.0 |
| | DI water | 1207 | | | | | |

TABLE 2-continued

Examples 1-8 and Comparative Examples 1-2

| | Precursor | | | | | Sol | |
|---|---|---|---|---|---|---|---|
| | Components | Wt (grams) | Solids Percent | Temp (° C.) | Time (hours) | Oxides | Mole Percent |
| Example 7 | Zr Acetate | 170 | 19 | 225 | 4 | $ZrO_2$ | 97.1 |
| | Y Acetate | 4.012 | | | | $Y_2O_3$ | 1.9 |
| | La Acetate | 2.125 | | | | $La_2O_3$ | 1.0 |
| | DI water | 162.86 | | | | | |
| Example 8 | Zr Acetate | 170 | 19 | 225 | 4 | $ZrO_2$ | 97.4 |
| | Y Acetate | 3.4 | | | | $Y_2O_3$ | 1.7 |
| | La Acetate | 2.125 | | | | $La_2O_3$ | 1.0 |
| | DI water | 166.55 | | | | | |

TABLE 3

Characterization of Examples 1-8 and Comparative Examples 1-2

| Example | M Intensity | M size (nm) | C/T intensity | C/T size (nm) | % C/T | XRD Average Size (nm) | Volume Average nm | Z-Average nm |
|---|---|---|---|---|---|---|---|---|
| Comparative Example 1 | 21 | 4.3 | 100 | 9.4 | 61 | 7.4 | 21.11 | 30.52 |
| Comparative Example 2 | 10 | 5.4 | 100 | 18.3 | 60 | 13.1 | 21.28 | 38.31 |
| Example 1 | 14 | 4.2 | 100 | 12.4 | 64 | 9.4 | 29.36 | 47.8 |
| Example 2 | 7 | 5.5 | 100 | 10.4 | 63 | 8.6 | 48.5 | 66 |
| Example 3 | ND | | 100 | 9.0 | 100 | 9.0 | 20.97 | 46 |
| Example 4 | ND | | 100 | 8.5 | 100 | 8.5 | 22.09 | 39.6 |
| Example 5 | ND | | 100 | 8.5 | 100 | 8.5 | | |
| Example 6 | | | | | | | | |
| Example 7 | | | | | | | | |
| Example 8 | | | | | | | | |

Comparison Examples 3 & 4 and Examples 9-12

Zirconia-based sols having particles with 2.1 to 2.2 mole percent $Y_2O_3$ with 0 to 3.0 mole percent $La_2O_3$ were prepared as described in Comparative Example 1 & 2 and Examples 1-4.

Each sol was dried at room temperature under flowing dry nitrogen and then crushed to a fine powder (100 mesh or smaller). Hot stage x-ray diffraction was used to determine the crystallite size of the predominant cubic/tetragonal phase after heating to successively higher temperatures as summarized in Table 4.

TABLE 4

Crystallite size as function of $La_2O_3$ Concentration

| | Mole Percent | Cubic/Tetragonal Crystallite Size (nanometers) | | | |
|---|---|---|---|---|---|
| | $La_2O_3$ | 900° C. | 1000° C. | 1100° C. | 1200° C. |
| Comparative 3 | 0 | 22 | 42 | 87 | 118 |
| Comparative 4 | 0.25 | 19 | 25 | 54 | 94 |
| Example 9 | 0.5 | 20 | 24 | 43 | 79 |
| Example 10 | 1.0 | 16 | 21 | 31 | 55 |
| Example 11 | 2.0 | 13 | 17 | 24 | 48 |
| Example 12 | 3.0 | 12 | 15 | 23 | 54 |

The effects of $La_2O_3$ additions in restricting grain growth are evident, especially at temperatures above 1000° C. Increasing the amount of $La_2O_3$ above 1.0 mole percent had little effect on the grain size.

Comparison Example 5

A partially sintered zirconia-based material commercially available under the trade designation "LAVA" (LAVA zirconia block 60 mm) from 3M ESPE (Saint Paul, Minn.) was removed from a 3-unit LAVA Frame (obtained from 3M ESPE). The cylindrical block was diced into wafers 1 millimeter in thickness with a low speed diamond saw using de-ionized water as a lubricant. The wafers were dried at 60° C. and then sintered by heating at a rate of 10° C./minute to 1500° C., holding at 1500° C. for 2 hours, and cooling at 10° C./minute to 20° C.

One of the sintered wafers was crushed and screened to −50, +100 mesh (300 to 150 micrometers). The granules were viewed at 50 times magnification with incident light. This provided a comparison standard (FIG. 2b) which was used to evaluate the relative translucency of sintered granules prepared from zirconia-based sols that contained particles doped with lanthanum and yttrium.

Comparison Example 6

A partially sintered zirconia-based material commercially available under the trade designation "LAVA" (LAVA zirconia block 60 mm) from 3M ESPE (Saint Paul, Minn.) was removed from a 3-unit LAVA Frame (obtained from 3M ESPE). The cylindrical block was diced into wafers 1 millimeter in thickness with a low speed diamond saw using de-ionized water as a lubricant. The wafers were dried at 60° C. and then sintered by heating at a rate of 2° C./minute to 600° C., holding at 600° C. for 30 minutes, heating at a rate of 7.5° C./minute to 1500° C., holding at 1500° C. for 2 hours, and then cooling at 10° C./minute to 20° C.

Cross-sections of one of the wafers were obtained by focused ion beam milling and used to determine the volume percent porosity. The volume percent porosity was calculated from the ratio of the pore area of the sintered body to the total area of the sintered body in electron micrographs. A representative image is shown in FIG. 1. The average porosity was 0.33 volume percent. This corresponds 99.7 percent of the theoretical density.

Example 13

A zirconia-based sol containing 2.2 mole percent $Y_2O_3$ and 3.0 mole percent $La_2O_3$ was prepared as described in Example 5. The sol was concentrated by osmosis. More specifically, the sol was placed in a membrane (Spectra/Por 1, Product Number 132655, MWCO 6000-8000 from Spectrum Laboratories Inc. (Rancho Dominguez, Calif.)). The membrane tubing was tied into a knot at the bottom while a movable twist-tie closure was used to seal the top just above the liquid sol. The loaded membrane was placed into an aqueous solution of polyethylene glycol having a weight average molecular weight of 20,000 grams/mole. This solution contained 600 grams polyethylene glycol per liter and the pH was 3.0. Water from the sol diffused through the membrane and into the aqueous solution of polyethylene glycol resulting in the drying of the sol to a rigid gel. During the first several hours the upper twist-tie was moved about once every half hour to compensate for the loss of water through the membrane. This prevented excessive collapse of the membrane and helped maintain the cylindrical shape of the membrane container. Once the sol had formed a semi-rigid gel it was allowed to stand overnight. The consolidated gel was removed from the dialysis bag and dried at 60° C. in air. The gel broke apart during drying into small chunks several millimeters in size.

A portion of the dry gel was crushed and screened to size −35, +60 mesh (500 to 250 micrometers). This material was then sintered in air by heating at a rate of 2° C./minute to 600° C., holding at 600° C. for 30 minutes, heating at a rate of 7° C./minute to 1200° C., holding at 1200° C. for 1 hour, and then cooling at 10° C./minute to 20° C.

Figure 2A:
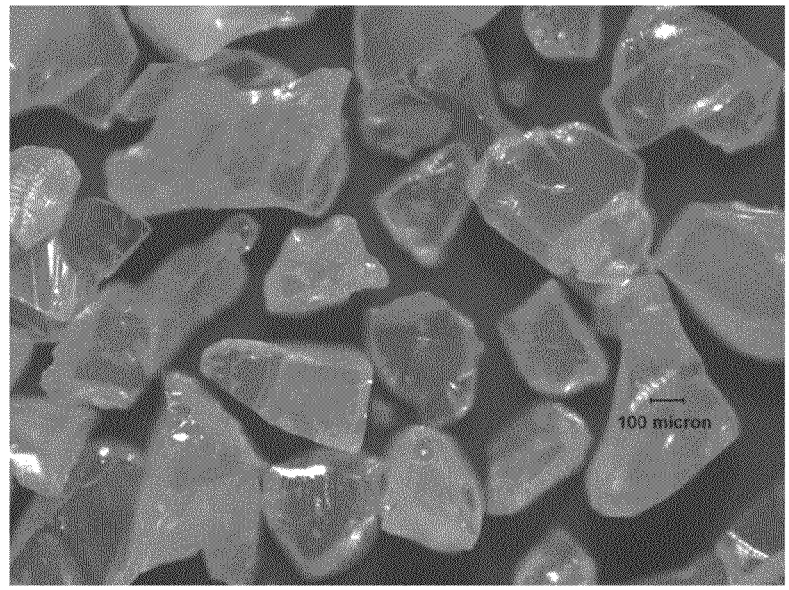
FIG. 2a shows sintered bodies of Example 13 viewed at 50 times magnification with incident light.
Figure 2B:
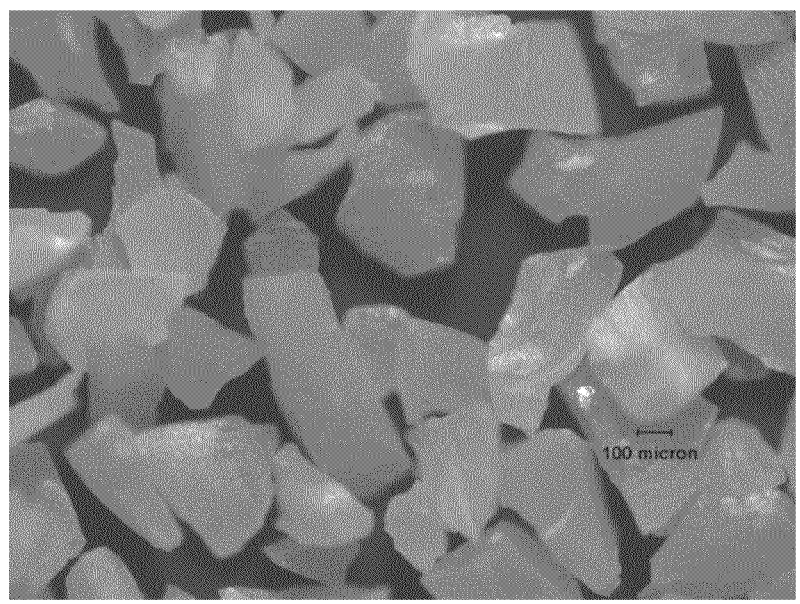
FIG. 2b shows sintered bodies of Comparative Example 5 viewed at 50 times magnification with incident light.

FIG. 2a shows the $La_2O_3$ doped material from this example. FIG. 2b shows Comparative Example 5, crushed and screened to about the same size. Both materials were viewed at 50 times magnification with incident light.

Figure 3:
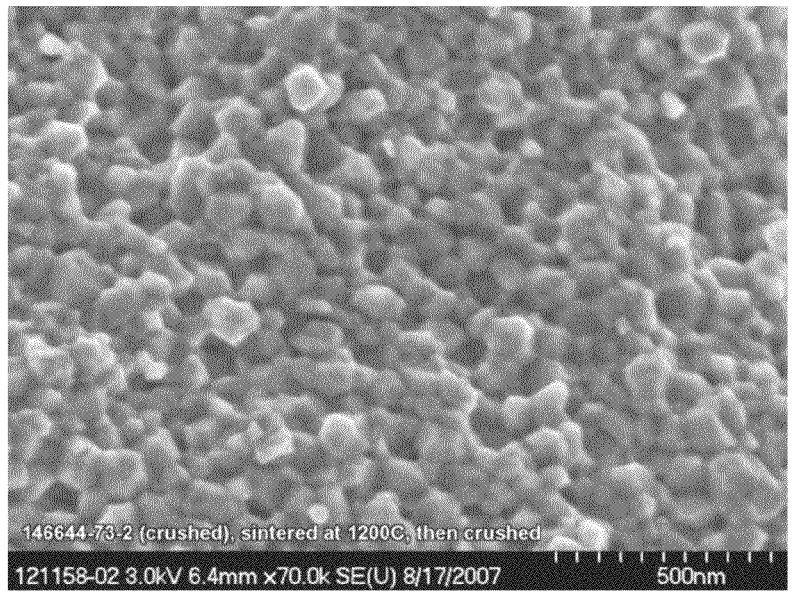
FIG. 3 is a field emission scanning micrograph of a fracture surface for a sintered body of Example 13.

FIG. 3 shows an FESEM micrograph of a fracture surface from one of the doped granules of Example 13. The material appears fully dense. The grain size determined by line intercept analysis of the micrograph was 99 nanometers.

Figure 4:
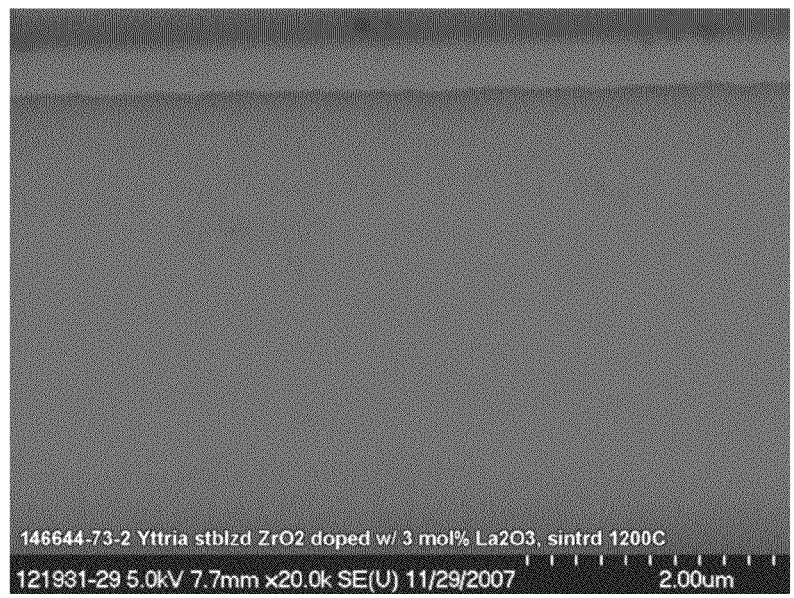
FIG. 4 is a field emission scanning micrograph of an ion-milled cross section of a sintered body of Example 13.

Cross-sections of the La-doped granules were obtained by focused ion beam milling and were used to determine the volume percent porosity. No pores were observed in any of the sections indicating a pore volume of essentially zero percent. A representative image is shown in FIG. 4. The light gray band at the top of the micrograph is the upper surface of the wafer. The darker gray below this corresponds to the vertical milled section.

Example 14a-b

Some of the sintered granules from Example 13 were reheated to 1300° C. (Example 14a) and 1400° C. (Example 14b). The sintered granules were heated at a rate of 10° C./minute to 1300° C. for Example 14a (or 1400° C. for Example 14b), held for 1 hour at that temperature, and then cooled at a rate of 10° C./minute to 20° C.

Figure 5A:
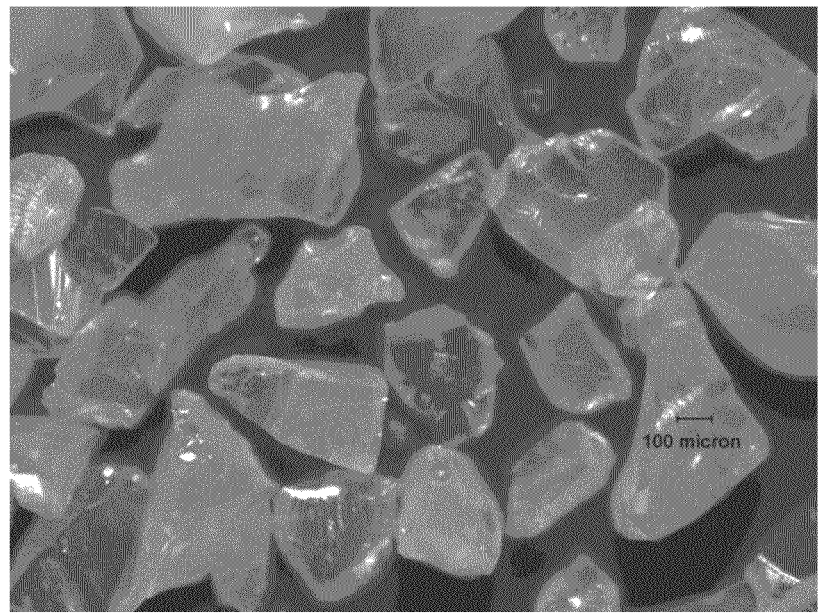
FIG. 5a shows sintered bodies of Example 13.
Figure 5B:
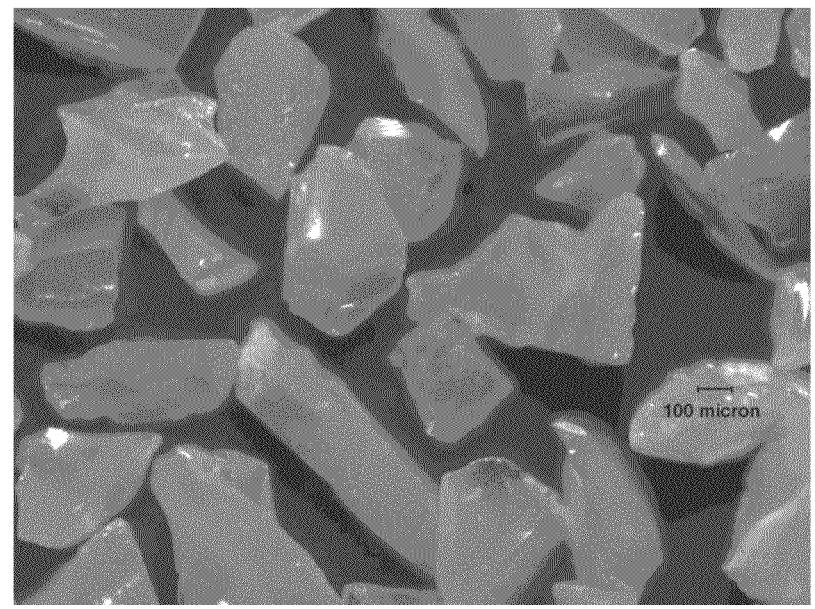
FIG. 5b shows sintered bodies of Example 14a, and FIG. 5c shows sintered bodies of Example 14b viewed at 50 times magnification with incident light.
Figure 5C:
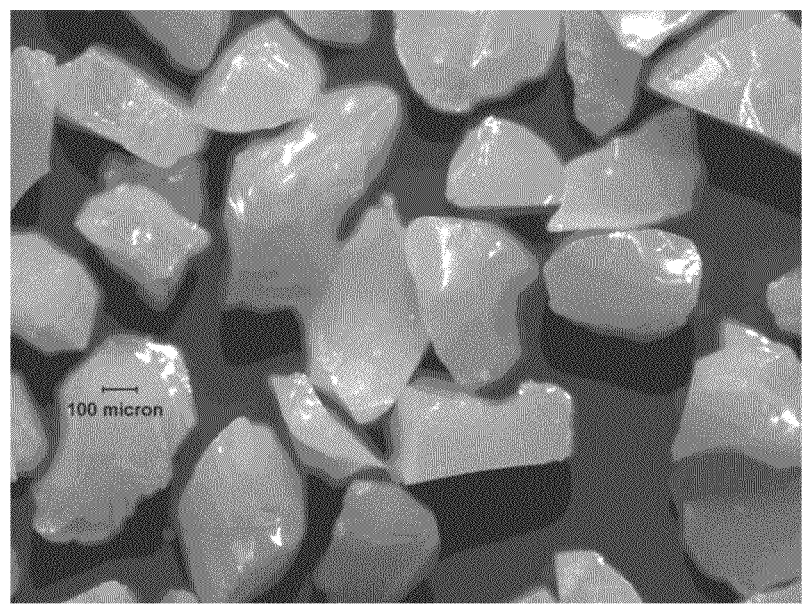

The grain size of each sample was determined by line intercept analysis of FESEM micrographs of the surfaces. The grain sizes of the samples after heating to 1300° C. and 1400° C. were 116 nanometers and 183 nanometers, respectively. Since the granules from Example 13 are already fully dense any change in translucency can be attributed to the grain size. As can be seen in FIGS. 5a, 5b, and 5c, even a small increase in grain size above 100 nanometers can reduce the translucency. FIG. 5a is for Example 13. FIG. 5b is for Example 14a that was reheated at 1300° C. FIG. 5c is for Example 14b that was reheated at 1400° C.

Example 15a-15e

A zirconia-based sol containing 2.2 mole percent $Y_2O_3$ and 1.0 mole percent $La_2O_3$ was prepared as described in Example 6. The sol was concentrated to a solid by osmosis. It was contained in a membrane (Spectra/Por 1, Product Number 132655, MWCO 6000-8000, Spectrum Laboratories Inc. (Rancho Dominguez, Calif.)). The membrane tubing was tied into a knot at the bottom. The top of the tubing was attached to the bottom of a small funnel which acted as a reservoir for the sol. The funnel and membrane were loaded with sol and then placed into an aqueous solution of polyethylene glycol having a weight average molecular weight of 20,000 grams/mole. This solution contained 600 grams polyethylene glycol per liter and the pH was 3.0. The funnel-membrane assembly was inserted to the point where the membrane was completely immersed in the polyethylene glycol solution. As water from the sol diffused out into the polyethylene glycol solution, additional sol entered the membrane from the reservoir until a solid cylinder of gel was obtained. Once the membrane was filled with a semi-rigid gel it was removed from the polyethylene glycol solution. Slow drying of the gel in a vented container was used in an attempt to make large pieces of dry gel. The consolidated gel was removed from the dialysis bag and placed in a 45 ml plastic jar with a 3 mm diameter hole in the cap. A piece of crumpled tissue paper was placed above and below the gel to cushion it during handling. The container was placed in an oven at 50° C. After 7 days the gel had formed several large cracks. At this point the jar cap was removed and drying was continued for 2 days. The gel had broken apart into chunks a few millimeters in size.

A portion of the dry gel was crushed and screened to −35, +60 mesh (500 to 250 micrometers). The gel granules were then sintered at different temperatures by heating in air.

The samples were sintered by heating at a rate of 2° C./min to 600° C., holding at 600° C. for 30 minutes, heating at a rate of 7° C./min to temperature T where T was 1000° C. (Example 15a), 1050° C. (Example 15b), 1100° C. (Example 15c), 1150° C. (Example 15d), or 1200° C. (Example 15e), holding at temperature T for 1 hour, and then cooling at a rate of 10° C./minute to 20° C.

Figure 6A:
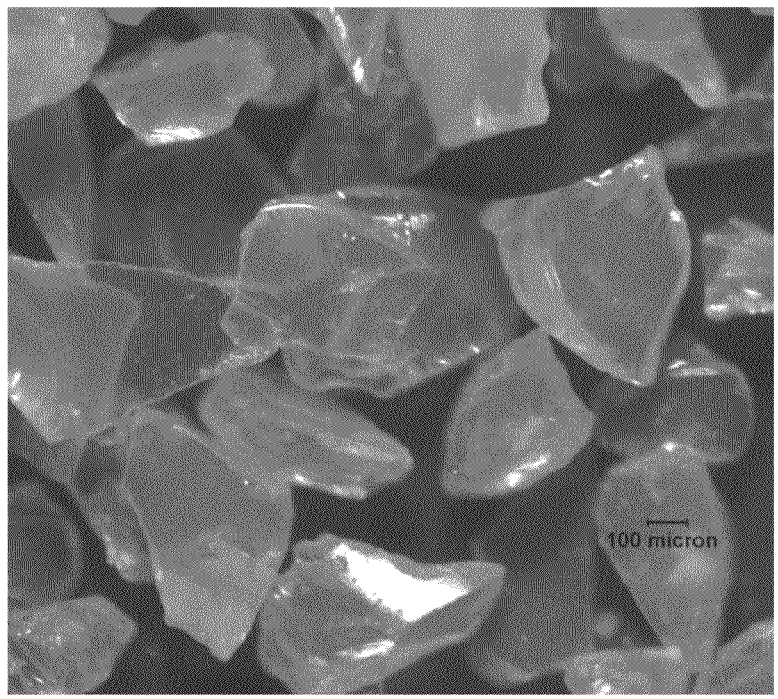
FIG. 6a shows sintered bodies of Example 15a viewed at 50 times magnification with incident light.
Figure 6B:
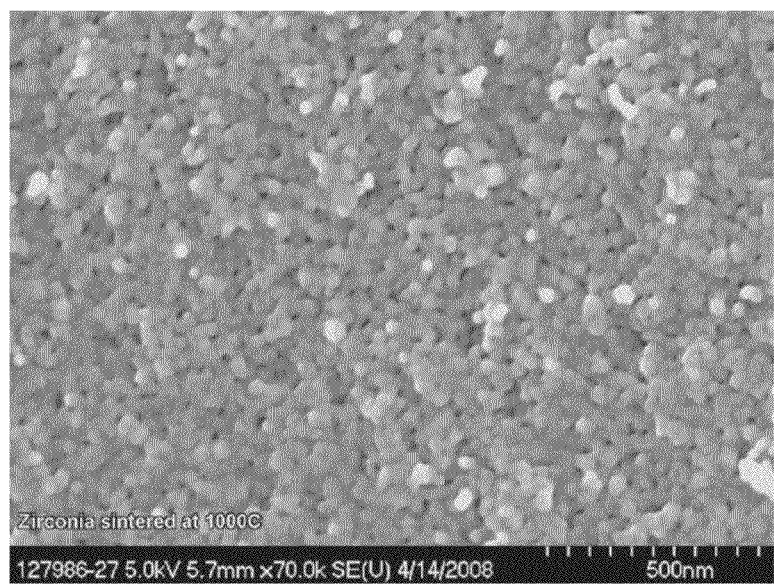
Figure 7A:
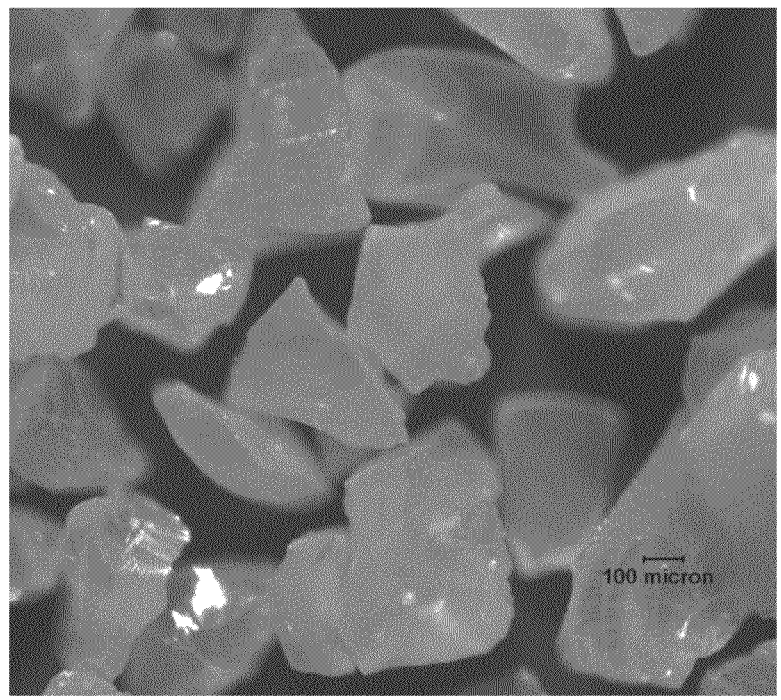
FIG. 7a shows sintered bodies of Example 15b viewed at 50 times magnification with incident light.
Figure 7B:
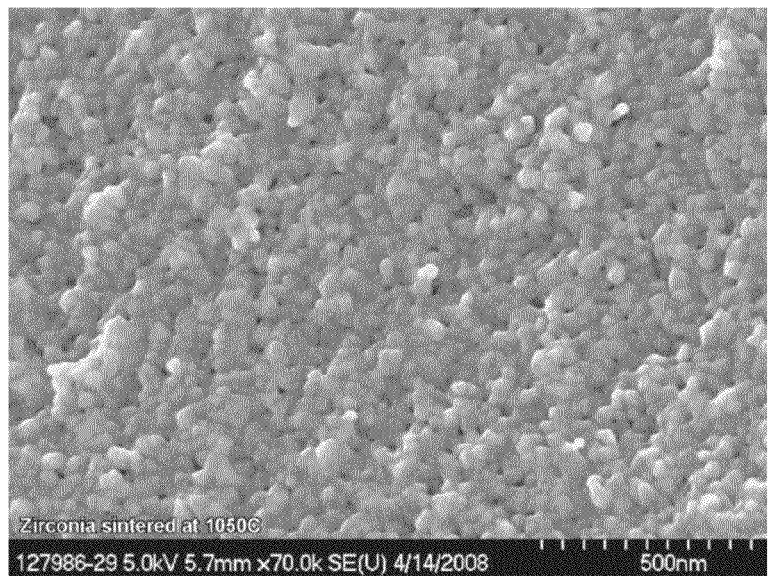
FIG. 7b is a field emission scanning micrograph of a fracture surface for a sintered body of Example 15b.
Figure 8A:
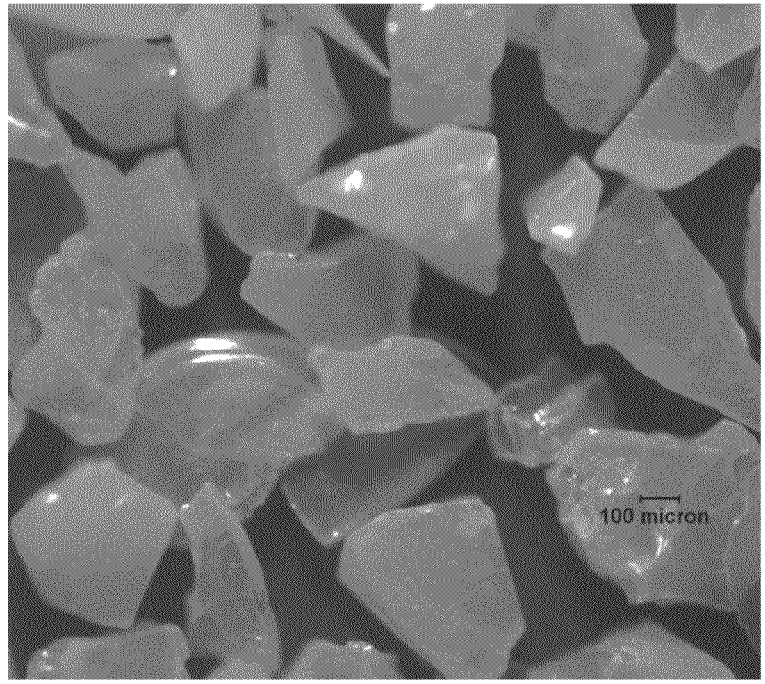
FIG. 8a shows sintered bodies of Example 15c viewed at 50 times magnification with incident light.
Figure 8B:
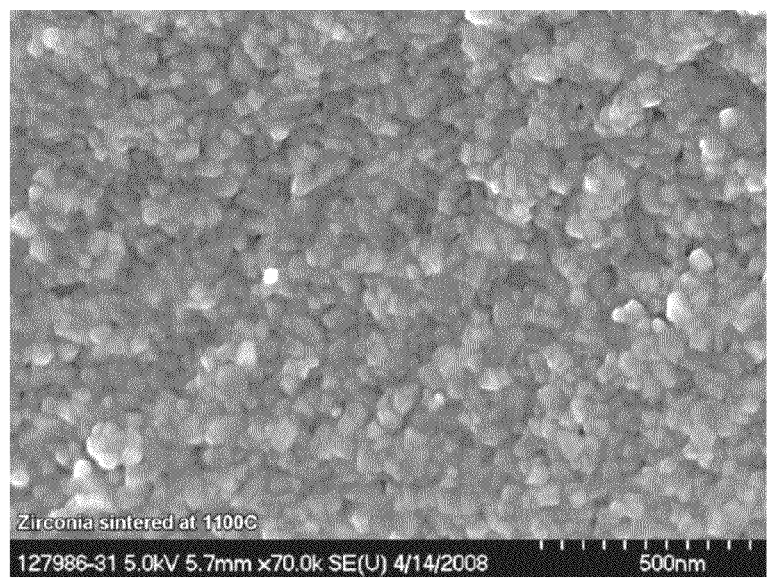
FIG. 8b is a field emission scanning micrograph of a fracture surface for a sintered body of Example 15c.
Figure 9A:
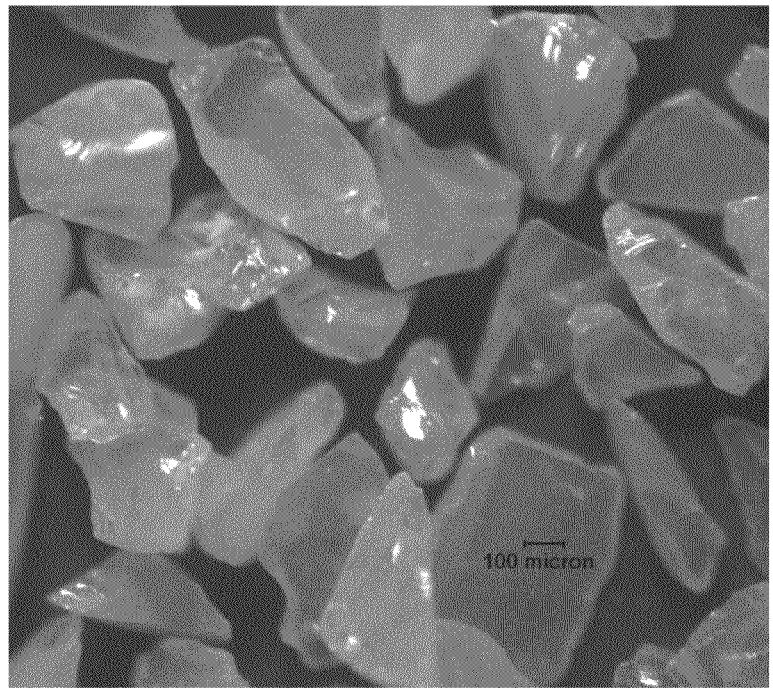
FIG. 9a shows sintered bodies of Example 15d viewed at 50 times magnification with incident light.
Figure 9B:
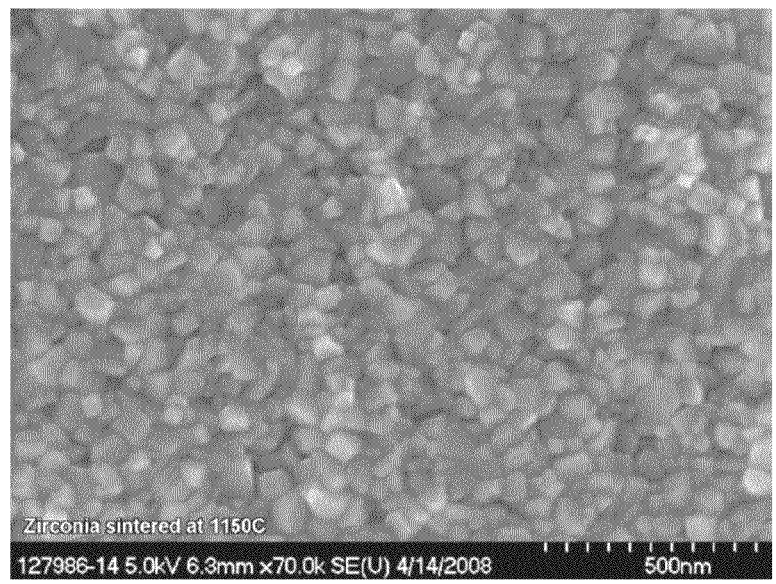
FIG. 9b is a field emission scanning micrograph of a fracture surface for a sintered body of Example 15d.
Figure 10A:
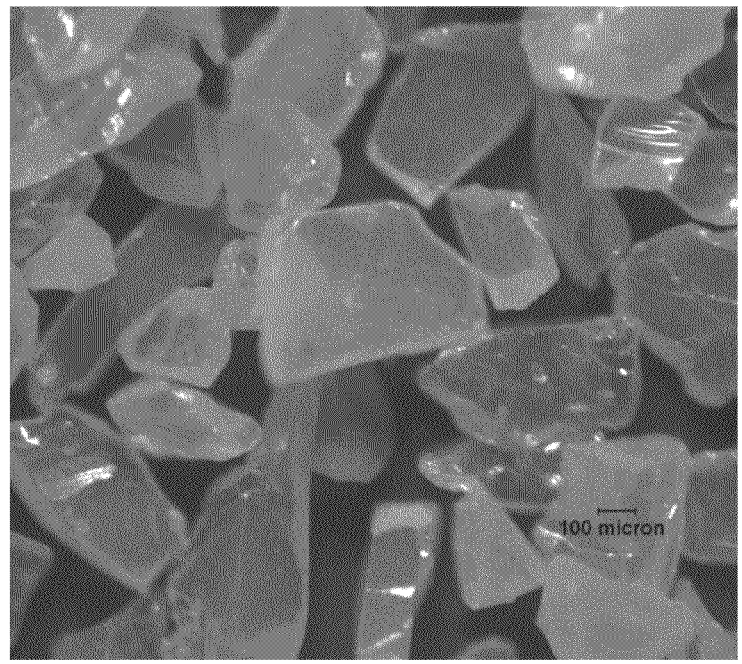
FIG. 10a shows sintered bodies of Example 15e viewed at 50 times magnification with incident light.
Figure 10B:
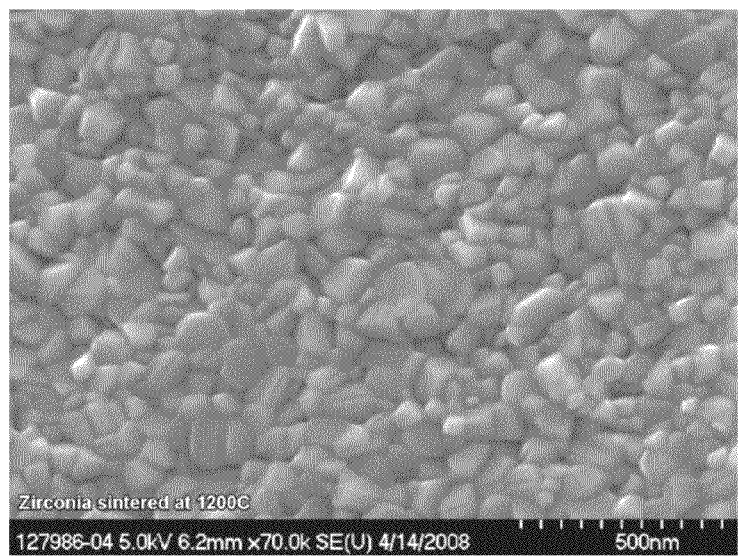
FIG. 10b is a field emission scanning micrograph of a fracture surface for a sintered body of Example 15e.

Micrographs of the sintered granules were obtained in incident light for visual comparison. The granules were also examined by FESEM and the average grain size was determined. The material sintered at 1000° C. is quite clear in appearance, but FESEM revealed that the material contained many small pores. The average grain size was 49 nm and the pores were less than half that size. Apparently the pores are small enough and uniformly dispersed so that there is little light scattering. As the sintering temperature increases to 1050° C. and 1100° C., the material becomes cloudy in appearance with little change in either the pore size or the average grain size (50 and 64 nanometers, respectively). It may be that as pores are eliminated, some areas are cleared faster and a difference in the effective refractive index of the areas of different density leads to scattering. Materials sintered at 1150° C. and 1200° C. have a larger average grain size (80 and 102 nanometers, respectively) but few pores remain and the observed clarity improves. The changes in microstructure are shown in FIGS. 6 to 10. More specifically, FIG. 6a shows the granules magnified 50 times using incident light and FIG. 6b shows the FESEM of a fracture surface magnified 70,000 times for Example 15a sintered at 1000° C. FIG. 7a shows the granules magnified 50 times using incident light and FIG. 7b shows the FESEM of a fracture surface magnified 70,000 times for Example 15b sintered at 1050° C. FIG. 8a shows the granules magnified 50 times using incident light and FIG. 8b shows the FESEM of a fracture surface magnified 70,000 times for Example 15c sintered at 1100° C. FIG. 9a shows the granules magnified 50 times using incident light and FIG. 9b shows the FESEM of a fracture surface magnified 70,000 times for Example 15d sintered at 1150° C. FIG. 10a shows the granules magnified 50 times using incident light and FIG. 10b shows the FESEM of a fracture surface magnified 70,000 times for Example 15e sintered at 1200° C.

Comparison Example 7

A partially sintered zirconia-based material commercially available under the trade designation "LAVA" (LAVA zirconia block 60 mm) from 3M ESPE (Saint Paul, Minn.) was removed from a 3-unit LAVA Frame (obtained from 3M ESPE). The cylindrical block was diced into wafers 2 mm in thickness with a low speed diamond saw using de-ionized water as a lubricant. The wafers were dried at 60° C. then sintered. The wafers were sintered by heating at a rate of 7.5° C./minute to 1500° C., holding at 1500° C. for 2 hours, and then cooling at 10° C./minute to 20° C.

One wafer was crushed and screened to −100, +200 mesh (150 to 75 micrometers). The average grain size was determined by line intercept analysis of fracture surfaces. The percentage of monoclinic phase before and after crushing was estimated by x-ray diffraction. This was used as a measure of the degree of transformation that occurred during fracture. The data is shown in Table 5 below.

Example 16

Pieces of the as-dried gel from Example 13, and some of the −35, +60 (500 to 250 micrometers) sized gel granules from Example 13 (zirconia with 2.3 mole percent $Y_2O_3$ and 3.0 mole percent $La_2O_3$) were sintered by heating in air. More specifically, the material was sintered by heating at a rate of 2° C./minutes to 600° C., holding for 30 minutes at 600° C., heating at a rate of 7° C./minutes to 1200° C., hold at 1200° C. for 1 hour, and then cooling at a rate of 10° C./minutes to 20° C.

The gel that had been pre-sized before sintering was used to determine the amount of monoclinic phase in the as-sintered material. The pieces that had not been pre-sized were crushed after sintering and screened to −100, +200 mesh (150 to 75 micrometers).

X-ray diffraction was used to compare the amount of monoclinic phase in the as-sintered material to the amount in the material crushed after sintering. The difference was used as a measure of the degree of transformation which occurred during fracture. The data is shown in Table 4 below.

Examples 17-18

Zirconia-based sols containing 1.0 mole percent $La_2O_3$ with 1.9 mole percent $Y_2O_3$ (Example 17) or 1.0 mole percent $La_2O_3$ plus 1.7 mole percent $Y_2O_3$ (Example 18) were prepared as described in Example 7 and 8.

The sols were concentrated to a solid by osmosis. The sol was contained in a membrane (Spectra/Por 1, Product Number 132655, MWCO 6000-8000, Spectrum Laboratories Inc. (Rancho Dominguez, Calif.)). The membrane tubing was tied into a knot at the bottom. The top of the tubing was attached to the bottom of a small funnel which acted as a reservoir for the sol. The funnel and membrane were loaded with sol and then placed into an aqueous solution of polyethylene glycol having a weight average molecular weight of 20,000 grams/mole. This solution contained 300 grams polyethylene glycol per liter and the pH was 3.0. The funnel-membrane assembly was inserted to the point where the membrane was completely immersed in the polyethylene glycol solution. As water from the sol diffused out into the polymer solution additional sol entered the membrane from the reservoir until a solid cylinder of gel was obtained. Once the membrane was filled with a semi-rigid gel it was removed from the polyethylene glycol solution. The gels were dried in an oven at 50° C. During drying the gels cracked and broke apart into pieces several mm in size.

A portion of the dry gel was crushed and screened to size −35, +60 mesh (500 to 250 micrometers). Pieces of the as-dried gels and some of the −35, +60 mesh (500 to 250 micrometers) sized gels were sintered by heating in air at a rate of 2° C./minute to 1200° C., holding at 1200° C. for 1 hour, and then cooling at a rate of 10° C./minute to 20° C.

The gels that had been pre-sized before sintering were used to determine the amount of monoclinic phase in the as-sintered material. The pieces that had not been pre-sized were crushed after sintering and screened to −100, +200 mesh (150 to 75 micrometers).

X-ray diffraction was used to compare the amount of monoclinic phase in the as-sintered material to the amount in the material crushed after sintering. The difference was used as a measure of the degree of transformation which occurred during fracture. The data is shown in Table 5 below.

TABLE 5

Characterization of Grain Size and Crystalline Phases

| | Comparison Example 7 | Example 16 | Example 17 | Example 18 |
|---|---|---|---|---|
| $Y_2O_3$ (mole percent) | 3.0 | 2.3 | 1.9 | 1.7 |
| $La_2O_3$ (mole percent) | 0.0 | 3.0 | 1.0 | 1.0 |
| Grain Size (nm) | 602 | 99 | 135 | 191 |
| Percent Monoclinic (as sintered) | 0 | 0 | 0 | 0 |
| Percent Monoclinic (crushed) | 7 | 1 | 8 | 24 |

The amount of transformation and the grain size were both reduced with increasing $Y_2O_3$ content. The optimum level of $Y_2O_3$ may depend on the application. Improved toughening would require lower levels of $Y_2O_3$, while higher translucency which is dependent on small grains would suggest higher $Y_2O_3$ contents.

We claim:
1. A partially sintered body comprising a product formed by partially sintering zirconia-based particles that are crystalline, that have an average primary particle size no greater than 100 nanometers, and that comprise
   a) at least 92.5 mole percent zirconium oxide based on total moles of inorganic oxide in the zirconia-based particles;
   b) at least 0.5 mole percent lanthanum oxide based on total moles of inorganic oxide in the zirconia-based particles;

c) at least 1.5 mole percent yttrium oxide based on total moles of inorganic oxide in the zirconia-based particles, wherein the partially sintered body comprises 25 to 75 volume percent inorganic oxide and 25 to 75 volume percent voids based on a total volume of the partially sintered body.

2. The partially sintered body of claim 1, wherein the partially sintered body comprises 0 to less than 5 volume percent organic material, water, or a combination thereof.

3. The partially sintered body of claim 1, wherein the partially sintered body comprises 40 to 70 volume percent inorganic oxide and 30 to 60 volume percent voids.

4. The partially sintered body of claim 1, wherein the zirconia-based particles comprise 92.5 to 98.0 mole percent zirconium oxide based on total moles of inorganic oxide in the zirconia-based particles, 0.5 to 5.0 mole percent lanthanum oxide based on total moles of inorganic oxide in the zirconia-based particles, and 1.5 to 2.5 mole percent yttrium oxide based on total moles of inorganic oxide in the zirconia-based particles.

5. The partially sintered body of claim 1, wherein at least 70 percent of the zirconia-based particles have a cubic/tetragonal crystalline structure.

* * * * *

UNITED STATES PATENT AND TRADEMARK OFFICE
CERTIFICATE OF CORRECTION

PATENT NO.        : 8,969,227 B2
APPLICATION NO.   : 14/065622
DATED             : March 3, 2015
INVENTOR(S)       : James Mathers It is certified that error appears in the above-identified patent and that said Letters Patent is hereby corrected as shown below:

In the Specification

<u>Column 3</u>
Line 24, delete "stoichiometeric" and insert -- stoichiometric --, therefor.

<u>Column 8</u>
Line 64, delete "(ZrO2)," and insert -- ($ZrO_2$), --, therefor.

<u>Column 9</u>
Line 45, delete "autogeneous" and insert -- autogenous --, therefor.

<u>Column 20</u>
Line 17, delete "monoclininc" and insert -- monoclinic --, therefor.

Line 31, delete "Pan" and insert -- Parr --, therefor.

<u>Column 22</u>
Line 53 (Approx.), Table 2, Example 3, delete "(ZrO2)" and insert -- ($ZrO_2$) --, therefor.

Signed and Sealed this
Fourth Day of August, 2015

Michelle K. Lee
*Director of the United States Patent and Trademark Office*